United States Patent
Persson

(10) Patent No.: US 10,139,354 B2
(45) Date of Patent: Nov. 27, 2018

(54) SPECTRAL X-RAY IMAGING

(71) Applicant: PRISMATIC SENSORS AB, Stockholm (SE)

(72) Inventor: Mats Persson, Vasterhaninge (SE)

(73) Assignee: PRISMATIC SENSORS, Stockholm (SE)

( * ) Notice: Subject to any disclaimer, the term of this patent is extended or adjusted under 35 U.S.C. 154(b) by 82 days.

(21) Appl. No.: 15/302,397

(22) PCT Filed: Apr. 7, 2014

(86) PCT No.: PCT/SE2014/050428
§ 371 (c)(1),
(2) Date: Oct. 6, 2016

(87) PCT Pub. No.: WO2015/156711
PCT Pub. Date: Oct. 15, 2015

(65) Prior Publication Data
US 2017/0023496 A1 Jan. 26, 2017

(51) Int. Cl.
*G06K 9/00* (2006.01)
*G01N 23/046* (2018.01)
(Continued)

(52) U.S. Cl.
CPC ........... *G01N 23/046* (2013.01); *A61B 6/032* (2013.01); *A61B 6/482* (2013.01); *A61B 6/5205* (2013.01);
(Continued)

(58) Field of Classification Search
CPC . G06T 11/005; G06T 2211/408; G01T 1/171; G01T 1/24; A61B 6/03
(Continued)

(56) References Cited

U.S. PATENT DOCUMENTS 5,727,041 A  3/1998 Hsieh
7,551,710 B2  6/2009 Abe et al.
(Continued)

FOREIGN PATENT DOCUMENTS

CN  102135606  7/2011
CN  102999917  3/2013
(Continued)

OTHER PUBLICATIONS

Firsching et al.: "Quantitative Material Reconstruction in CT wit Spectroscopic X-ray Pixel Detectors a Simulation Study", 2000 IEEE Nuclear Science Symposium Conference Record, San Diego, CA, USA, XP031534978.
(Continued)

Primary Examiner — Charlotte M Baker
(74) Attorney, Agent, or Firm — Young & Thompson

(57) ABSTRACT

There is provided a method for processing a radiographic image acquired with at least two energy levels. A first step (S1) involves providing energy-resolved image data representative of the radiographic image with at least two energy levels, e.g. from a detector or from an intermediate storage. A second step (S2) involves decomposing the provided image data into at least one basis image representation, based on a model where a combination of at least two basis functions is used to express a representation of at least one linear attenuation coefficient, and where at least one basis function models a physical material and at least one other basis function models the Non-Linear Partial Volume, NLPV, effect.

9 Claims, 13 Drawing Sheets

(51) Int. Cl.
  G01N 23/04    (2018.01)
  G01N 23/087   (2018.01)
  A61B 6/00     (2006.01)
  G06T 11/00    (2006.01)
  G06T 7/00     (2017.01)
  A61B 6/03     (2006.01)
(52) U.S. Cl.
  CPC ......... *G01N 23/04* (2013.01); *G01N 23/087* (2013.01); *G06T 7/0012* (2013.01); *G06T 11/005* (2013.01); *A61B 6/03* (2013.01); *A61B 6/52* (2013.01); *G06T 2207/10081* (2013.01); *G06T 2207/30004* (2013.01); *G06T 2211/408* (2013.01)
(58) Field of Classification Search
  USPC .............. 382/131; 378/4, 5, 901, 98.12; 250/370.09; 703/2
  See application file for complete search history.

(56) References Cited

U.S. PATENT DOCUMENTS

| | | | |
|---|---|---|---|
| 7,778,380 B2 | 8/2010 | Altman et al. | |
| 8,165,264 B2* | 4/2012 | Zou | G06T 11/005 378/5 |
| 8,213,566 B2 | 7/2012 | Roessl et al. | |
| 8,615,120 B2 | 12/2013 | Proksa | |
| 2010/0189212 A1 | 7/2010 | Zou | |
| 2014/0278303 A1* | 9/2014 | Larimore | G06F 17/5095 703/2 |

FOREIGN PATENT DOCUMENTS

| | | | |
|---|---|---|---|
| EP | 2 146 321 A1 | 1/2010 | |
| WO | 2007034356 A2 | 3/2007 | |
| WO | 2008021664 A1 | 2/2008 | |
| WO | 2008135897 A2 | 11/2008 | |
| WO | 2013011418 A | 1/2013 | |
| WO | 2014/001984 A1 | 1/2014 | |

OTHER PUBLICATIONS

Glover G H; et al.: "Nonlinear partial volume artifacts in X-ray computed tomography", Medical Physics, XP002323197.
Nuyts et al: "Modelling the physics in the iterative reconstruction for transmission computed tomography", Physics in Medicine and Biology, vol. 58, No. 12, Bristol GB, pp. r63-r96, XP020246384, ISSN: 0031-9155.
Schirra et al.: "Statistical Reconstruction of Material Decomposed Data in Spectral CT", IEEE Transactions on Medical Imaging, XP011516353.
International Search Report, dated Jan. 12, 2015, from corresponding PCT application.
Markku J. Tapiovaara, et al., SNR and DQE analysis of broad spectrum X-ray imaging, Physics in Medicine & Biology, 1985, pp. 519-529, vol. 30, No. 6.
Robert E. Alvarez, et al., Energy-selective reconstructions in X-ray computerised tomography, Physics in Medicine & Biology, 1976, pp. 733-744, vol. 21, No. 5.
Peter M. Joseph, et al., The exponential edge-gradient effect in X-ray computed tomography, Physics in Medicine & Biology, 1981, pp. 473-487, vol. 26, No. 3.
Jeffrey A. Fessler, et al., Maximum-likelihood dual-energy tomographic image reconstruction, Medical Imaging 2002: Image Processing, May 9, 2002, pp. 38-49, Proceedings of SPIE vol. 4684.
Raz Carmi, et al., A Unique Noncathartic CT Colonography Approach by Using Two-Layer Dual-Energy MDCT and a Special Algorithmic Colon Cleansing Method, IEEE Nuclear Science Symposium Conference Record, Oct. 19-25, 2008, pp. 4780-4783.
Wenli Cai, et al., Low-dose dual-energy electronic cleansing for fecal-tagging CT colonography, Medical Imaging 2013: Computer-Aided Diagnosis, Mar. 18, 2013, pp. 86700W-1-86700W-9, Proceedings of SPIE vol. 8670.
J. W. Stayman, et al., Overcoming Nonlinear Partial Volume Effects in Known-Component Reconstruction of Cochlear Implants, Medical Imaging 2013: Physics of Medical Imaging, Mar. 19, 2013, pp. 86681L-1-86681L-6, Proceedings of SPIE vol. 8668.
Hui Xue, et al., A correction method for dual energy liquid CT image reconstruction with metallic containers, Journal of X-Ray Science and Technology, 2012, pp. 301-316, vol. 20.
E. Roessl, et al., K-edge imaging in x-ray computed tomography using multi-bin photon counting detectors, Physics in Medicine & Biology, 2007, pp. 4679-4696, vol. 52.
G.H. Glover, et al., Nonlinear partial volume artifacts in x-ray computed tomography, Medical Physics, May/Jun. 1980, pp. 238-248, vol. 7, Issue 3.
Katrien Van Slambrouck, et al., Metal artifact reduction in computed tomography using local models in an image block-iterative scheme, Medical Physics, Nov. 2012, pp. 7080-7093, vol. 39, Issue 11.
Dec. 21, 2017, EP communication issued for related EP application No. 14888575.9.
Chinese Official Action—201480077832.1—Jul. 4, 2018.

* cited by examiner

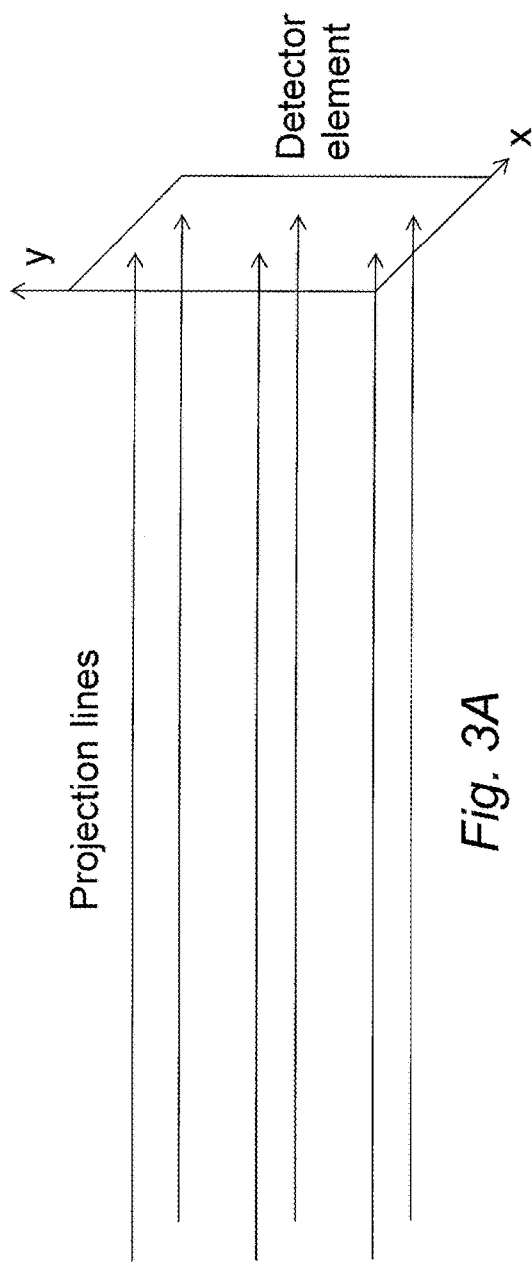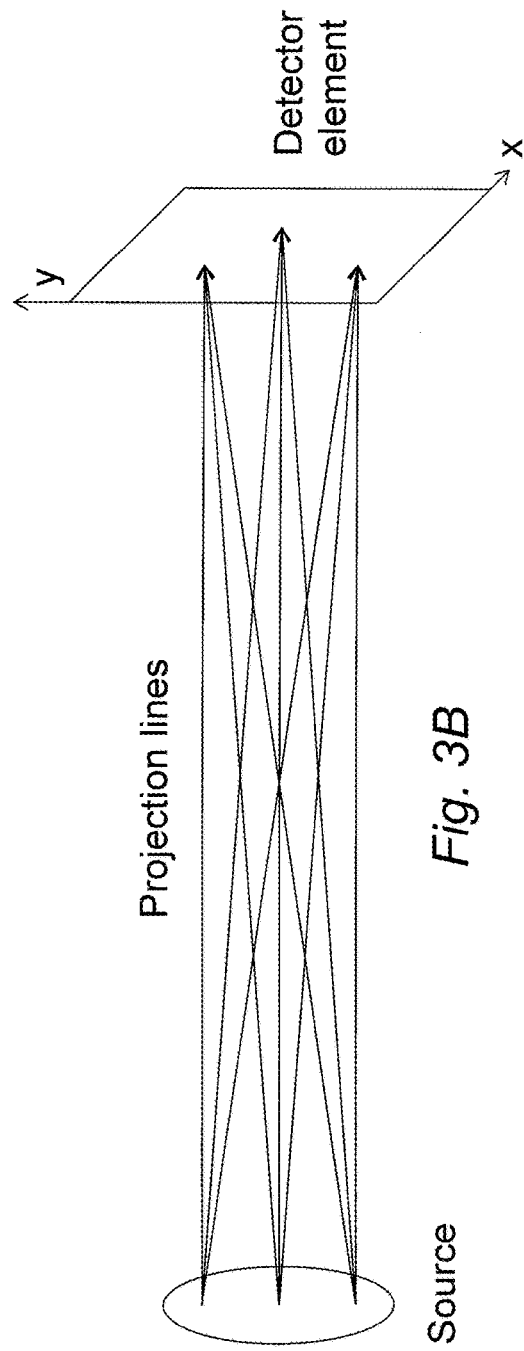
Fig. 3A
Fig. 3B

SPECTRAL X-RAY IMAGING

TECHNICAL FIELD

The proposed technology generally relates to radiographic imaging such as x-ray imaging and more specifically relates to a method and system for processing a radiographic image.

BACKGROUND

Radiographic imaging such as x-ray imaging has been used for years in medical applications and for non-destructive testing.

Normally, an x-ray imaging system includes an x-ray source and an x-ray detector consisting of multiple detector elements. The x-ray source emits x-rays, which pass through a subject or object to be imaged and are then registered by the detector. Since some materials absorb a larger fraction of the x-rays than others, an image is formed of the interior of the subject or object.

An x-ray computed tomography (CT) system includes an x-ray source and an x-ray detector arranged in such a way that projection images of the subject or object can be acquired in different view angles covering at least 180 degrees. This is most commonly achieved by mounting the source and detector on a support that is able to rotate around the subject or object. An image containing the projections registered in the different detector elements for the different view angles is called a sinogram. In the following, a collection of projections registered in the different detector elements for different view angles will be referred to as a sinogram even if the detector is two-dimensional, making the sinogram a three-dimensional image.

A further development of x-ray imaging is energy-resolved x-ray imaging, also known as spectral x-ray imaging, where the x-ray transmission is measured for several different energy levels. This can be achieved by letting the source switch rapidly between two different emission spectra, by using two or more x-ray sources emitting different x-ray spectra, or by using an energy-discriminating detector which measures the incoming radiation in two or more energy levels. One example of such a detector is a multi-bin photon-counting detector, where each registered photon generates a current pulse which is compared to a set of thresholds, thereby counting the number of photons incident in each of a number of energy bins.

A spectral x-ray projection measurement results in one projection image for each energy level. A weighted sum of these can be made to optimize the contrast-to-noise ratio (CNR) for a specified imaging task as described in Tapiovaara and Wagner, "SNR and DQE analysis of broad spectrum X-ray imaging", Phys. Med. Biol. 30, 519.

Another technique enabled by energy-resolved x-ray imaging is basis material decomposition. This technique utilizes the fact that all substances built up from elements with low atomic number, such as human tissue, have linear attenuation coefficients μ(E) whose energy dependence can be expressed, to a good approximation, as a linear combination of two basis functions:

$$\mu(E) = a_1 f_1(E) + a_2 f_2(E).$$

If there is one or more element in the imaged volume with high atomic number, high enough for a k-absorption edge to be present in the energy range used for the imaging, one basis function must be added for each such element. In the field of medical imaging, such k-edge elements can typically be iodine or gadolinium, substances that are used as contrast agents.

Basis material decomposition has been described in Alvarez and Macovski, "Energy-selective reconstructions in X-ray computerised tomography", Phys. Med. Biol. 21, 733. In basis material decomposition, the integral of each of the basis coefficients, $A_i = \int_l a_i dl$ for $i=1, \ldots, N$ where N is the number of basis functions, is inferred from the measured data in each projection ray 1 from the source to a detector element. In one implementation, this is accomplished by first expressing the expected registered number of counts in each energy bin as a function of $A_i$:

$$\lambda_i = \int_{E=0}^{\infty} S_i(E) \exp\left(-\sum_{j=1}^{N} A_j f_j(E)\right) dE \qquad \text{Eq. 1}$$

Here, $\lambda_i$ is the expected number of counts in energy bin i, E is the energy, $S_i$ is a response function which depends on the spectrum shape incident on the imaged object, the quantum efficiency of the detector and the sensitivity of energy bin i to x-rays with energy E. Even though the term "energy bin" is most commonly used for photon-counting detectors, this formula can also describe other energy resolving x-ray systems such as multi-layer detectors or kVp switching sources.

Then, the maximum likelihood method may be used to estimate $A_i$, under the assumption that the number of counts in each bin is a Poisson distributed random variable. This is accomplished by minimizing the negative log-likelihood function, see Roessl and Proksa, K-edge imaging in x-ray computed tomography using multi-bin photon counting detectors, Phys. Med. Biol. 52 (2007), 4679-4696:

$$\hat{A}_1, \ldots, \hat{A}_N = \underset{A_1, \ldots, A_N}{\operatorname{argmin}} \sum_{i=1}^{M_b} \lambda_i(A_1, \ldots, A_N) - m_i \ln \lambda_i(A_1, \ldots, A_N) \qquad \text{Eq. 2}$$

where $m_i$ is the number of measured counts in energy bin i and $m_b$ is the number of energy bins.

When the resulting estimated basis coefficient line integral $\hat{A}_i$ for each projection line is arranged into an image matrix, the result is a material specific projection image, also called a basis image, for each basis i. This basis image can either be viewed directly (in projection x-ray imaging) or taken as input to a reconstruction algorithm to form maps of $a_i$ inside the object (in CT).

All x-ray imaging systems have finite resolution. The x-ray source has a finite width, and each detector element has a finite size, and this means that the number of photon counts measured by any detector element contains contributions from all possible sub-rays from points on the source to points on the detector. This means that a projection measurement which is made exactly on the interface between two materials will result in a measured attenuation which is intermediate between the attenuations of the two materials, which has the effect of blurring the image.

When viewing an image, either a projection image or a CT image, boundaries between regions with high and low signal intensity will therefore typically contain an interface region consisting of image pixels with intermediate signal intensity. The observer interpreting the image does not know whether these pixels represent a layer of intermediate attenuation between the two regions or if they contain a portion of a sharp interface.

SUMMARY

It is a general object to improve radiographic imaging such as x-ray imaging.

It is desirable to improve resolution in x-ray imaging without having to use smaller x-ray sources and detectors with smaller detector elements, which is expensive and technically challenging.

In particular, there is a need for differentiating sharp interfaces from gradual transitions in the image Furthermore, there is a need for measuring the position of interfaces as precisely as possible. For example, in the field of medical imaging it may be of interest to measure the width of a blood vessel, or the size of a tumor, or the volume of the heart.

It is a specific object to provide a method for processing a radiographic image acquired with at least two energy levels.

It is also a specific object to provide a system for processing a radiographic image acquired with at least two energy levels.

It is another object to provide an imaging system comprising such a system for processing a radiographic image.

Yet another object is to provide a corresponding computer program and computer program product.

These and other objects are met by embodiments of the proposed technology.

According to a first aspect, there is provided a method for processing a radiographic image acquired with at least two energy levels. The method comprises the step of providing energy-resolved image data representative of the radiographic image with at least two energy levels, from a detector or from an intermediate storage. The method further comprises the step of decomposing the provided image data into at least one basis image representation, based on a model where a combination of at least two basis functions is used to express a representation of at least one linear attenuation coefficient, where at least one basis function, also referred to as an ordinary basis function, models a physical material and at least one other basis function, also referred to as an NLPV basis function, models the Non-Linear Partial Volume, NLPV, effect.

By way of example, the provided image data may be an energy-resolved sinogram and the output may be at least one basis image corresponding to an NLPV basis function, also referred to as an NLPV basis image, or at least one subsequently reconstructed tomographic NLPV basis image, enabling the identification of interfaces.

In another example, the provided image data may be an energy-resolved sinogram and the output may be at least one basis image corresponding to an ordinary basis function, also referred to as an ordinary basis image which can subsequently be reconstructed to yield at least one tomographic ordinary basis image. For example, the tomographic ordinary basis image(s) may have a reduced level of NLPV artifacts compared to a tomographic basis image reconstructed from a basis image resulting from a basis material decomposition without NLPV basis. A mapping may be applied to at least one of the ordinary basis images resulting from the decomposition, before the basis image is reconstructed, resulting in at least one corrected ordinary basis image.

In yet another example, the provided image data may be an energy-resolved sinogram and the output image data may be a set of at least two tomographic basis images.

As an example, the energy-resolved image data may include image data of an energy-resolved projection image, an energy-resolved sinogram or an energy-resolved reconstructed tomographic image.

The method may for example be used for medical imaging or non-destructive testing.

According to a second aspect, there is provided a system for processing a radiographic image acquired with at least two energy levels. The system is configured to obtain energy-resolved image data representative of the radiographic image with at least two energy levels. The system is also configured to perform basis decomposition of said image data into at least one basis image representation, based on a model where a combination of at least two basis functions is used to express a representation of at least one linear attenuation coefficient, where at least one basis function, also referred to as an ordinary basis function, models a physical material and at least one other basis function, also referred to as an NLPV basis function, models the Non-Linear Partial Volume, NLPV, effect.

According to a third aspect, there is provided an imaging system comprising such a system for processing a radiographic image.

According to a fourth aspect, there is provided a computer program comprising instructions, which when executed by at least one processor, cause the processor(s) to provide energy-resolved image data representative of a radiographic image acquired with at least two energy levels, and perform basis decomposition of the provided image data into at least one basis image representation by using at least one ordinary basis function modeling a physical material and at least one basis function modeling the Non-Linear Partial Volume, NLPV, effect.

According to a fifth aspect, there is provided a computer program product comprising a computer-readable storage medium carrying such a computer program.

BRIEF DESCRIPTION OF THE DRAWINGS

FIGS. 3A-B are schematic diagrams illustrating an example of the coordinate system used in the mathematical description of the NLPV effect as well as two different discretizations of an extended beam: (A) discrete parallel rays; and (B) a representation of both the source and the detector as a finite number of points, with one projection line between each source-detector point pair.

DETAILED DESCRIPTION

Figure 1:
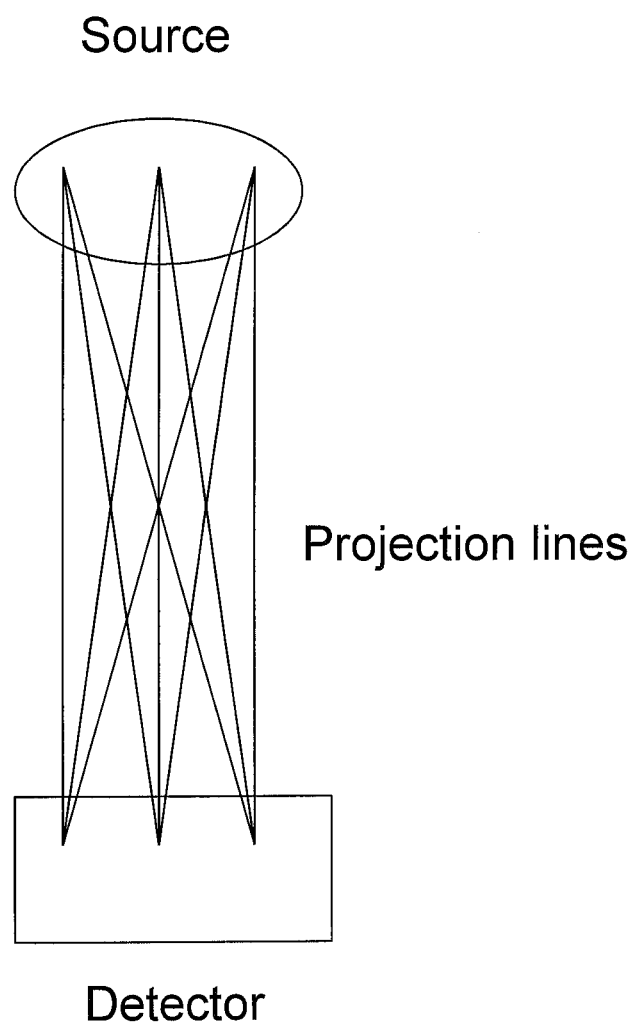
FIG. 1 is a schematic drawing of the imaging geometry with finite source and detector element width.

Before the description of the invention itself, it may be useful to begin with a brief overview of the Non-Linear Partial Volume, NLPV, effect. This effect arises in projection x-ray imaging and computed tomography when the source or the detector element (or both) is extended, i.e. not point-like. The x-ray intensity which is measured by the x-ray element is the integral of the intensity over all projection lines from the source to the detector, as shown in the example of FIG. 1.

Figures 2A, 2B, 2C:
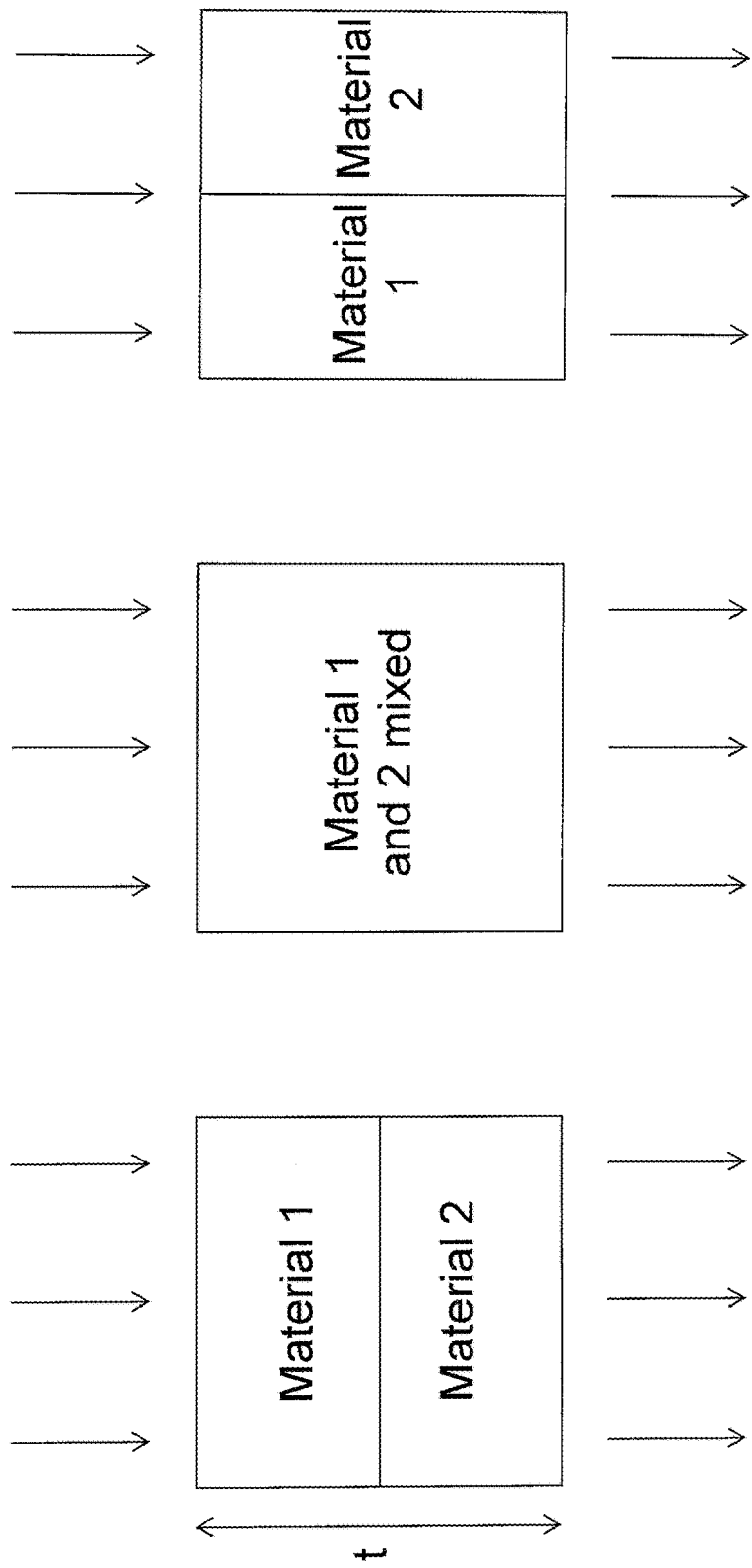
FIGS. 2A-C is a set of schematic diagrams illustrating the Non-Linear Partial Volume, NLPV, effect.

In order to demonstrate how the NLPV effect arises, consider the idealized situation when the source is point-like and located far from the object while the detector is extended, so that the rays from the source to the detector are essentially parallel. In the situation illustrated in FIGS. 2A-C, the x-rays traverse a volume containing two materials with different linear attenuation coefficients $\mu_1$ and $\mu_2$. Assume that all the x-rays passing through the volume are measured by a single detector element. If the x-rays pass one material first and then the other, as illustrated in FIG. 2A, the number of transmitted photons will be $$N_0 \exp\left(-\frac{t}{2}(\mu 1 + \mu 2)\right)$$

where $N_0$ is the incident number of photons and t is the volume thickness. In FIG. 2B, the volume contains a homogeneous mixture of the two materials. The transmission here is the same as in FIG. 2A, since each x-ray passes through a thickness t/2 of each material and the exponential form of the attenuation means that the order in which the two materials are traversed does not matter. In FIG. 2C, however, the interface is parallel to the beam so that half the detector is hit by x-rays having passed material 1 and the other half is hit by x-rays having passed material 2. The transmitted number of photons is therefore $$\frac{N_0}{2}(\exp(-\mu_1 t) + \exp(-\bar{\mu}_2 t)),$$

i.e. different from FIGS. 2A-B.

This effect is called the Non-Linear Partial Volume, NLPV, effect or the exponential edge-gradient effect, because the exponential form of x-ray attenuation makes the measured transmission a non-linear function of the attenuation coefficients of the constituent materials. It has been studied in Glover and Pelc, "Nonlinear partial volume artifacts in x-ray computed tomography", Med. Phys. 7 (3) 238-48 (May-June 1980) and in Joseph and Spital, "The exponential edge-gradient effect in x-ray computed tomography", Phys. Med. Biol. 26(3):473-87 (May 1981).

If polychromatic x-rays are used, N0, μ1 and μ2 are functions of energy. In case A and B, the detector measures an exponentially attenuated beam with effective attenuation coefficient $$\frac{t}{2}(\mu_1(E) + \mu_2(E))$$

which lies in the two-dimensional function space spanned by $\mu_1(E)$ and $\mu_2(E)$. However, the transmission in case C cannot be expressed as the exponential of a function in that two-dimensional space. Thus, even if the attenuation coefficients of all substances in the human body are assumed to be linear combinations of two basis functions, the NLPV effect breaks the two-dimensionality if there are interfaces parallel to the beam direction.

Consider an x-ray projection measurement with a single detector element as shown in FIG. 3A. Assume that N basis functions are sufficient to describe the attenuation coefficients of all materials in the imaged volume in the absence of the NLPV effect and let $A_1(x,y), \ldots, A_N(x,y)$ be the basis coefficient line integrals along the projection line with coordinates (x,y). Sometimes, these basis coefficient line integrals are referred to as basis projections. Also, make the simplifying assumption that the rays from source to detector are parallel (which is true in the limit of a point-like source located far from the detector). The total number of photons incident on the detector element is the integral of the incident photon fluence over the detector element:

$$\lambda_i = \frac{1}{D} \int \int \int_{E=0}^{\infty} S_i(E) \exp\left(-\sum_{j=1}^{N} A_j(x,y) f_j(E)\right) dE\, dx\, dy \qquad \text{Eq. 3}$$

Here, the outer integral is taken over the surface of the detector element, with area D. By letting an overline denote the average of a quantity over the detector:

$$\bar{g} = \frac{1}{D} \int \int g(x,y) dx\, dy \qquad \text{Eq. 4}$$

this can be rewritten as:

$$\lambda_i = \int_{E=0}^{\infty} S_i(E) \overline{\exp\left(-\sum_{J=1}^{N} A_J f_J(E)\right)} dE \qquad \text{Eq. 5}$$

A new basis function can be defined as:

$$f_{NLPV}(E) = -\ln\overline{\exp\left(-\sum_{J=1}^{N} A_j(x,y)f_J(E)\right)} - \sum_{j=1}^{N} \overline{A}_j f_j(E) \quad \text{Eq. 6}$$

where $\overline{A}_i = \iint A_i(x,y)dxdy$. A basis function constructed in this way will be called an NLPV basis function in the following.

Eq. 5 can then be written as:

$$\lambda_i = \int_{E=0}^{\infty} S_i(E)\exp\left(-\sum_{j=1}^{N} \overline{A}_j f_j(E) - f_{NLPV}(E)\right)dE \quad \text{Eq. 7}$$

This suggests modifying the basis material decomposition forward model (Eq. 1) to:

$$\lambda_i = \int_{E=0}^{\infty} S_i(E)\exp\left(-\sum_{j=1}^{N} A_j f_j(E) - A_{NLPV} f_{NLPV}(E)\right)dE \quad \text{Eq. 8}$$

where $f_{NLPV}$ is a basis function constructed according to Eq. 6. Note that $f_{NLPV}$ here is a fixed function, i.e. $A_i$ are not the same as the $A_i$ used to construct $f_{NLPV}$. In this formula, the N first basis functions suffice to describe measurements where all rays hitting the detector element are attenuated equally. The last basis function is needed to describe situations where the NLPV effect is present. Typically, Eq. 8 does not describe the forward model exactly, except for the precise choice of space-variant basis functions that was used to construct $f_{NLPV}$. However, it suffices that it describes the forward model approximately in order for $A_{NLPV}$ to be nonzero when the NLPV effect is present.

In the following, it will be described how this example framework can be used in practice to identify interfaces in the imaged volume. This description of the invention relates to medical x-ray imaging, but it will be appreciated that the invention also can be used for other applications, such as non-destructive testing.

In the following descriptions, it will also be assumed that a multi-bin photon-counting detector is used, although the invention is not limited to thereto.

Figure 4:
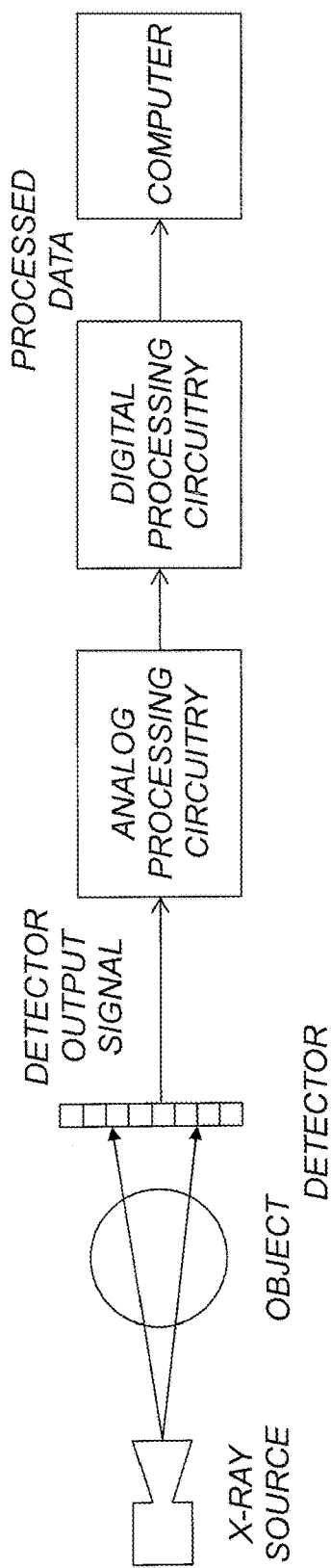
FIG. 4 is a schematic diagram illustrating an example of an x-ray imaging system.

As illustrated in the example of FIG. 4, an x-ray imaging system comprises an x-ray source, which emits x-rays; a detector, which detects the x-rays after they have passed through the object; analog processing circuitry, which processes the raw electrical signal from the detector and digitizes it; digital processing circuitry which may carry out further processing operations on the measured data such as applying corrections, storing it temporarily, or filtering; and a digital computer which stores the processed data and may perform further post-processing or reconstruction.

Figure 5:
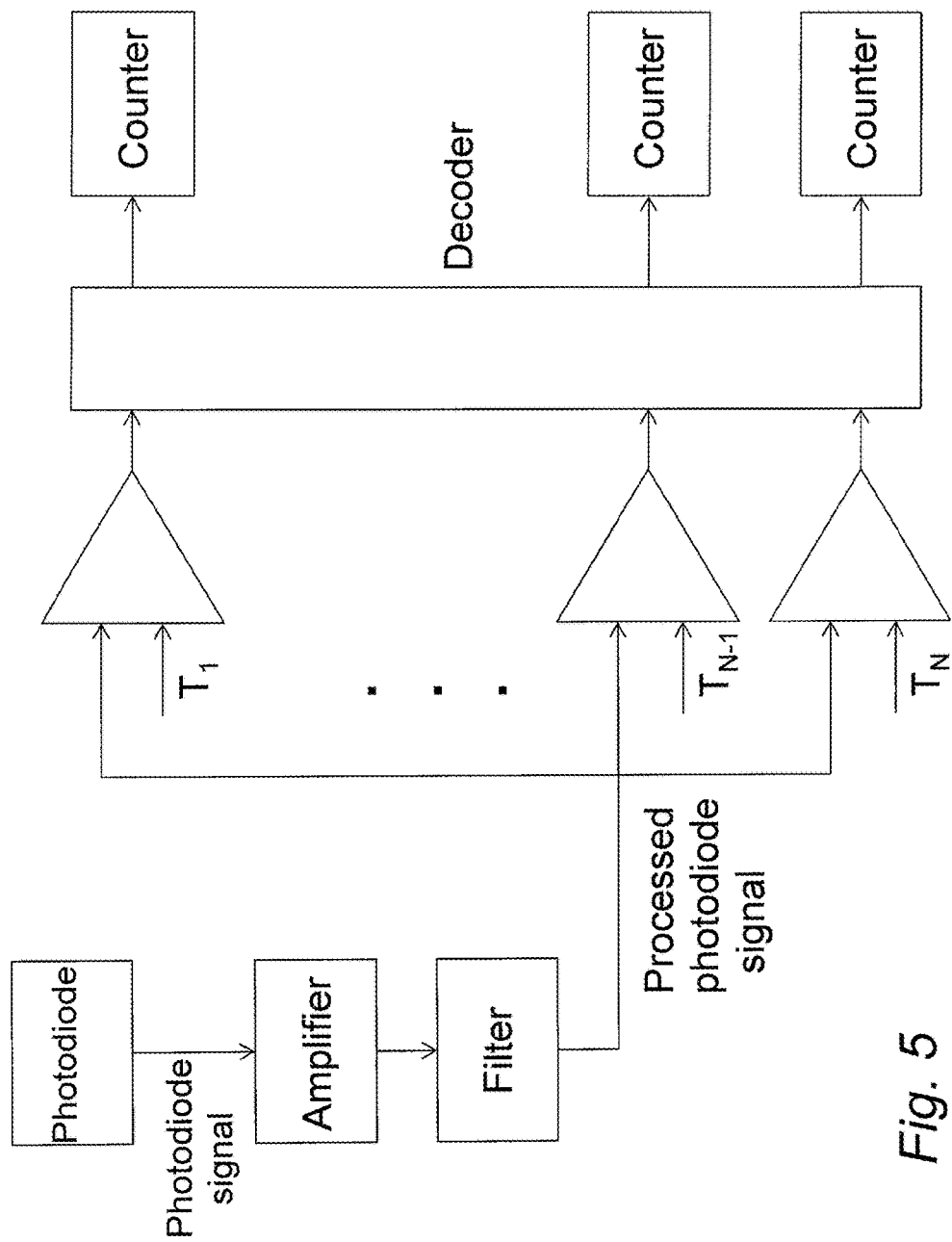
FIG. 5 is a schematic diagram illustrating an example of a photon-counting detector with several energy thresholds $T_1, \ldots, T_N$.
Figure 6:
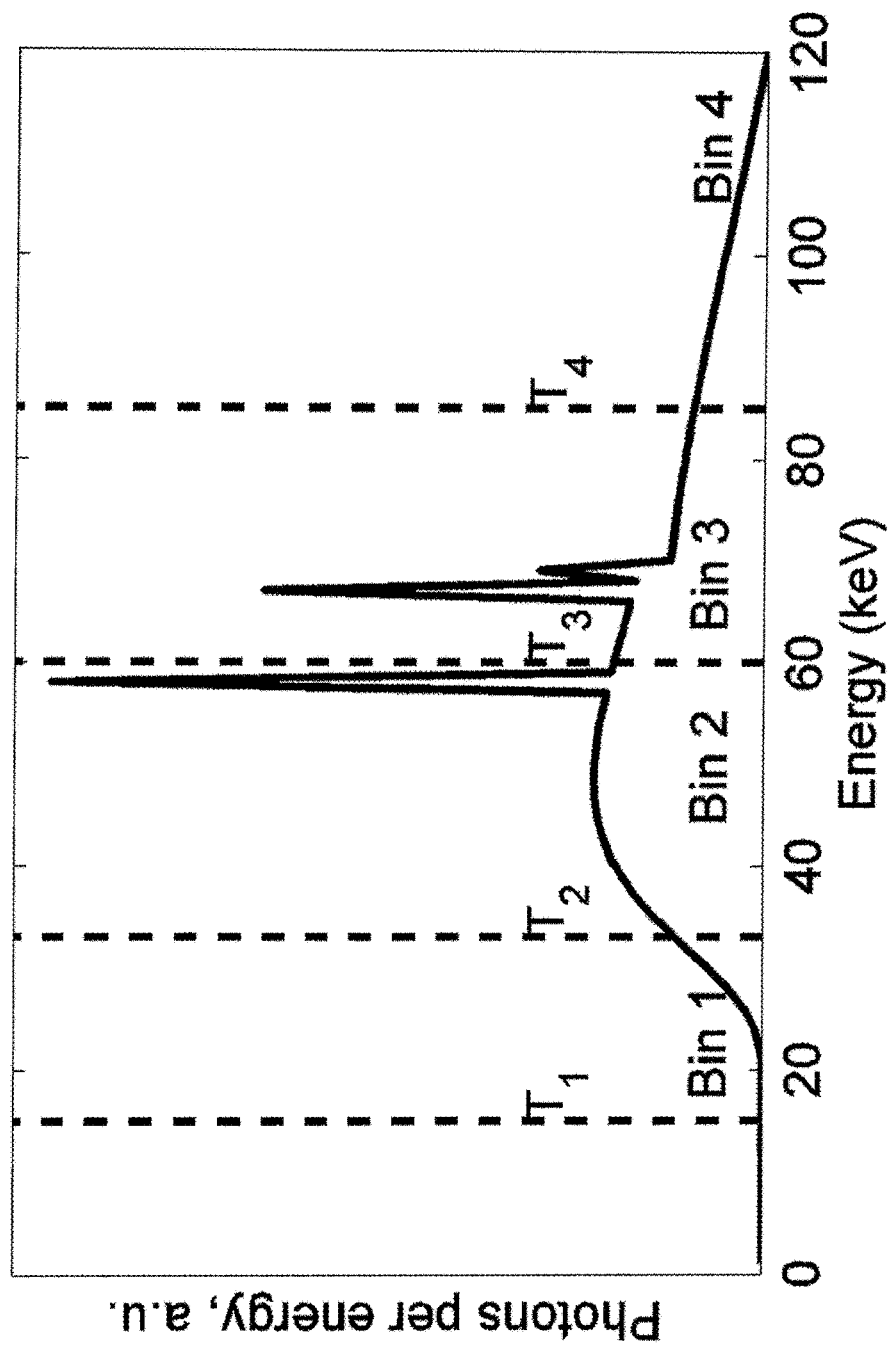
FIG. 6 is a schematic diagram illustrating an example of how a photon counting detector with several energy thresholds divides the spectrum into several energy bins.

In a particular example embodiment of the invention, the detector is a photon-counting detector as shown in FIG. 5 together with associated analog processing electronics. The detector includes a reverse-biased photodiode where the photons interact and generate current pulses which are amplified by an amplifier and further processed by a filter to attain a desired pulse shape. Each pulse is then compared to a number of thresholds $T_1, \ldots, T_{M_b}$ using comparators, and a decoder circuit processes the comparator output signals and increments one of several counters, corresponding to the highest threshold which is lower than the pulse height. In this way, the incident x-ray spectrum is divided into energy bins with one counter each counting the number of registered photons in that bin, as illustrated in FIG. 6. The counter values form the raw data that is read out from the detector and, possibly after further processing in the digital processing circuitry, stored by the computer.

Figure 7A:
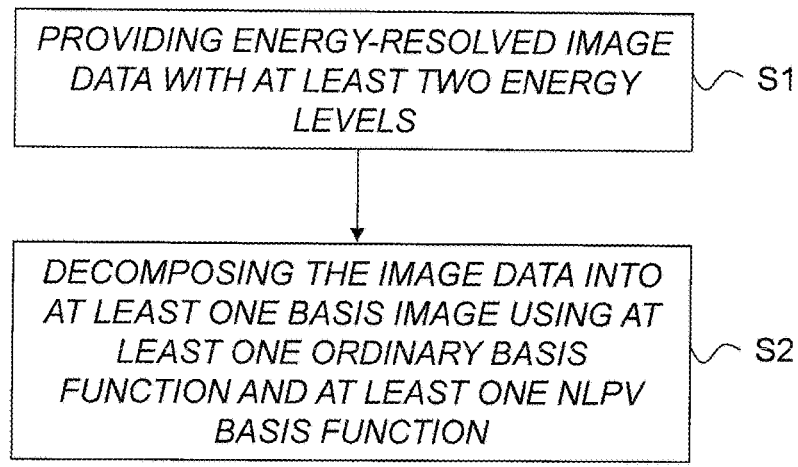
FIG. 7A is a schematic flow diagram illustrating an example of a method for processing a radiographic image acquired with at least two energy levels.

FIG. 7 is a schematic flow diagram illustrating an example of a method for processing a radiographic image acquired with at least two energy levels.

Step S1 involves providing energy-resolved image data representative of the radiographic image with at least two energy levels, e.g. from a detector or from an intermediate storage.

Step S2 involves decomposing the provided image data into at least one basis image representation, based on a model where a combination of at least two basis functions is used to express a representation of at least one linear attenuation coefficient, and where at least one basis function, also referred to as an ordinary basis function, models a physical material and at least one other basis function, also referred to as an NLPV basis function, models the Non-Linear Partial Volume, NLPV, effect.

Figure 7B:
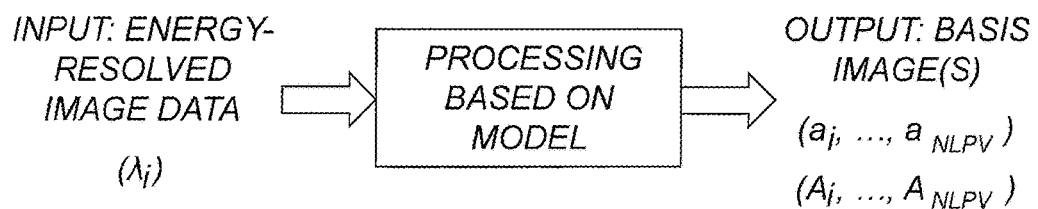
FIG. 7B is a schematic diagram illustrating an example of image processing based on a model, using energy-resolved image data as input and producing one or more basis image(s) as output.

FIG. 7B is a schematic diagram illustrating an example of image processing based on a model, using energy-resolved image data as input and producing one or more basis image(s) as output.

In a specific example, the energy-resolved image data includes a representation of the number of photons ($\lambda_1$) incident per detector element, and the model defines the number of photons incident per detector element as a function of i) basis coefficients ($a_j, \ldots, a_{NLPV}$) used to express the linear attenuation coefficient(s) or line integrals ($A_j, \ldots, A_{NLPV}$) of the basis coefficients, and ii) the at least two basis functions, and the decomposition comprises the step of estimating at least a subset of the basis coefficients or at least a subset of the line integrals of the basis coefficients to provide a representation of the at least one basis image.

In a particular non-limiting example, the least one other basis function that models the NLPV effect is constructed by:
  selecting a set of at least one ordinary basis function, such that the energy dependent linear attenuation coefficients of homogeneous materials in the image volume can be described by a linear combination of the basis functions in the set;
  determining the fraction of transmitted photons as a function of energy for a detector element situated behind an inhomogeneous region of materials, as seen from the source, taking into account the spatially extended nature of either the detector, the source or both; and
  constructing at least one NLPV basis function as the linear attenuation coefficient of a fictious material which, if one unit of distance of a homogeneous slab of this material were traversed by an x-ray beam, would give the same transmitted photon fraction as a function of energy as the calculated fraction which is transmitted through an inhomogeneous region.

By way of example, the provided image data may be an energy-resolved sinogram and the output may be at least one basis image corresponding to an NLPV basis function, also referred to as an NLPV basis image, or at least one subsequently reconstructed tomographic NLPV basis image, either of which enables the identification of interfaces.

For example, a mapping may be applied to at least one of the NLPV basis images resulting from the decomposition, resulting in a NLPV basis image approximately proportional to the traversed common path length of an interface.

As an example, the energy-resolved image data may be an energy-resolved sinogram and where initially a first basis material decomposition is made using a model without NLPV basis, resulting in a set of at least one basis image which is reconstructed to yield at least one tomographic basis image, which is replaced by zero in at least a subset of the image volume and forward projected to yield at least one sinogram of basis line integrals. Subsequently a second decomposition can be made using a model including at least one ordinary basis function and at least one NLPV basis function, where the line integrals of the model corresponding to at least one ordinary basis function are assumed to be equal to the sinogram of line integrals.

In another example, the provided image data may be an energy-resolved sinogram and the output may be at least one basis image corresponding to an ordinary basis function, also referred to as an ordinary basis image which is subsequently reconstructed to yield at least one tomographic ordinary basis image.

Preferably, the at least one tomographic ordinary basis image has a reduced level of NLPV artifacts compared to a tomographic basis image reconstructed from a basis image resulting from a basis material decomposition without NLPV basis.

For example, a mapping may be applied to at least one of the ordinary basis images resulting from the decomposition, before the basis image is reconstructed, resulting in at least one corrected ordinary basis image.

Preferably, the corrected basis image is a better estimate of the actual space average of a line integral of a basis coefficient over the extent of the beam than the original image.

In a particular example, the output basis image representation(s) may include at least one sinogram of ordinary basis coefficient line integrals and at least one sinogram of NLPV basis coefficient line integrals, and where subsequently a set of ordinary tomographic basis images corresponding to ordinary basis functions is computed by minimizing a penalized data discrepancy between the at least one sinogram of ordinary basis coefficient line integrals and the at least one sinogram of NLPV basis coefficient line integrals, on one side, and at least one sinogram of simulated ordinary basis coefficient line integrals obtained from a forward projection of the tomographic basis images, on the other side. The forward projection is for example calculated with at least two line integrals from the source to each detector element, yielding a spatially variant basis coefficient line integral for each detector element, and where a mapping is used to translate a representation of the spatially variant basis coefficient line integrals into the at least one sinogram of simulated ordinary basis coefficient line integrals and the at least one sinogram of NLPV basis coefficient line integrals.

For example, the basis image representation(s) may be defined on a subdivided voxel grid, obtained by reconstructing a preliminary image from the provided image data, selecting a region of interest where high image resolution is desired, calculating the gradient of the image data or a spatially filtered version of said image data and subdividing each voxel in the region of interest into slices by introducing slice interfaces orthogonal to the gradient direction.

In yet another example, the provided image data may be an energy-resolved sinogram and the output image data may be a set of at least two tomographic basis images.

For example, the tomographic basis images may be obtained by minimizing a penalized data discrepancy between the forward projection of the basis images and the energy-resolved sinogram.

The penalized data discrepancy minimization may be done, e.g. under the assumption that at least one of the tomographic basis images is equal to zero in at least a region of the image volume.

By way of example, the energy-resolved image data may include image data of an energy-resolved projection image, an energy-resolved sinogram or an energy-resolved reconstructed tomographic image.

The method is generally applicable and can be used, e.g. for medical imaging or non-destructive testing. The method may for example be used for medical imaging in at least one of the following medical or diagnostic applications: delineating bones, blood vessels, metal implants, tendons, muscles, colon content and white and gray brain matter, and identifying splinters of metal or bone.

As an example, the energy levels may be obtained by an energy discriminating detector, by using at last two x-ray sources with different acceleration voltages, or by x-ray tube voltage switching.

Figure 8:
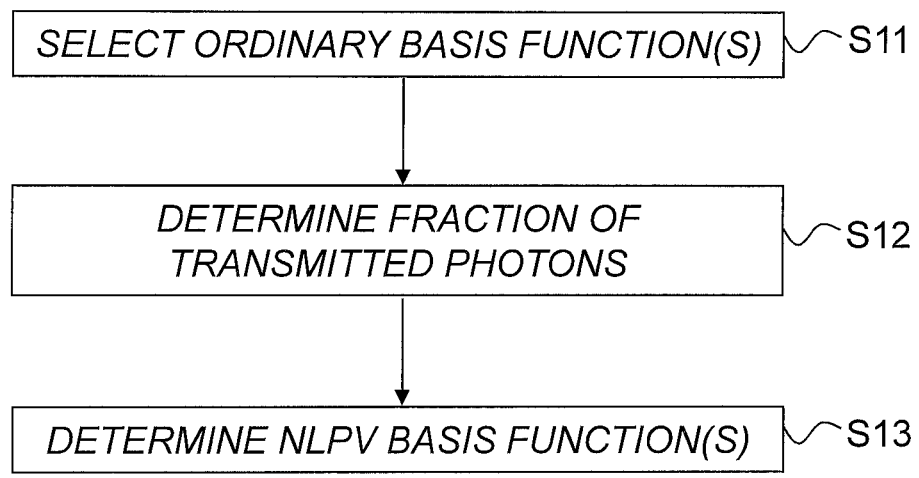
FIG. 8 is a schematic flow diagram illustrating an example of an algorithm for creating a set of basis functions which can be used in an algorithm that identifies interfaces.

FIG. 8 is a schematic flow diagram illustrating an example algorithm for creating a set of basis functions which can be used in an algorithm that identifies interfaces.

Step S11: A number of ordinary basis functions are selected as the attenuation coefficients of materials likely to be present in the image volume.

Step S12: The fraction transmitted photons as a function of energy is calculated for a detector element situated behind an inhomogeneous region, e.g. an interface, consisting of the materials considered in S11, as seen from the source.

Step S13: At least one new basis function, capturing the NLPV effect, is determined or constructed as the linear attenuation coefficient of a fictious material which, if one unit of distance of a homogeneous slab of this material were traversed by an x-ray beam, would give the same transmitted photon fraction as a function of energy as the one calculated in S12.

For example, the set of basis functions, comprising the ordinary basis functions selected in S11 together with the basis function constructed in S13, may be stored on a storage medium.

As an example, the step S12 of determining the fraction of transmitted photons may be performed based on measurement or simulation.

Figure 9:
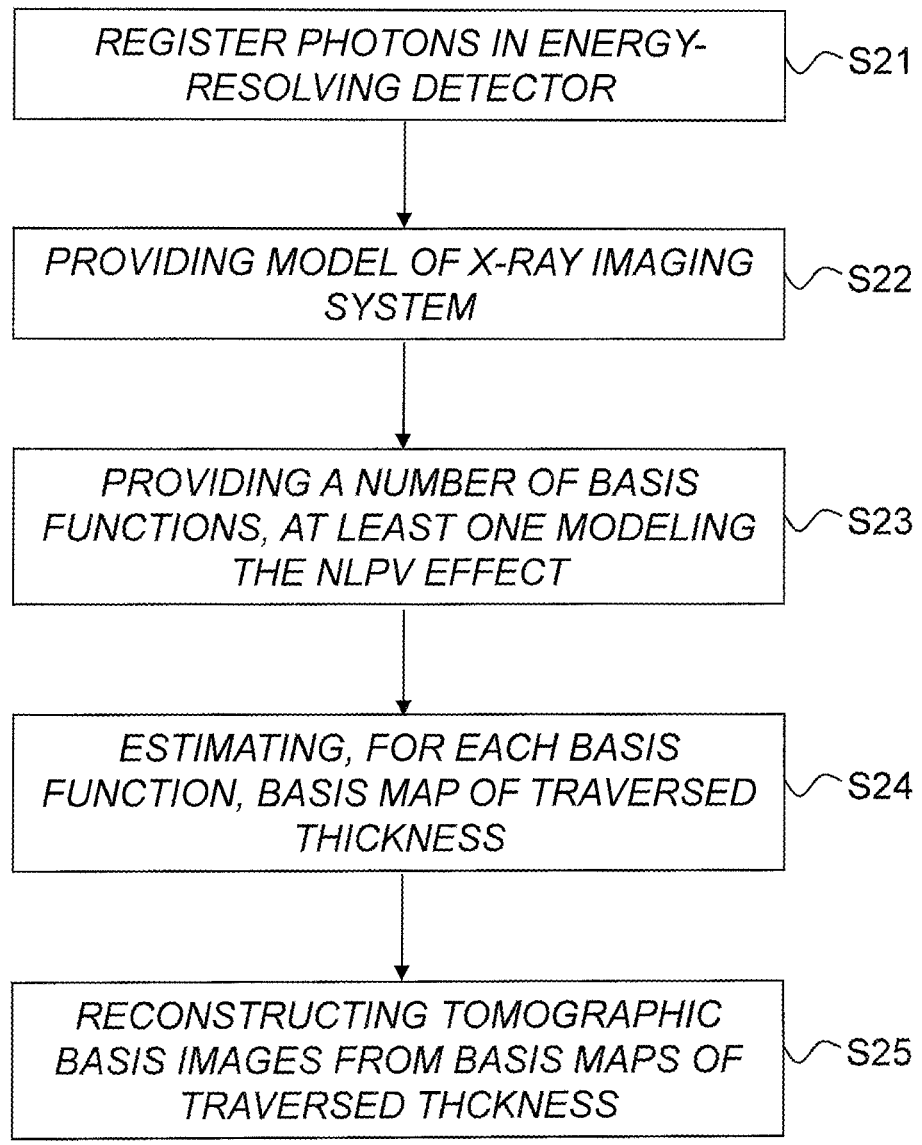
FIG. 9 is a schematic flow diagram illustrating an example of an algorithm for generating a NLPV image enabling the identification of interfaces.

FIG. 9 is a schematic flow diagram illustrating an example of an algorithm for generating a NLPV image enabling the identification of interfaces.

Step S21: Photons are registered in an energy-resolving detector, resulting in count numbers in each of several energy bins for each detector element. The counts are transferred to a data processing device.

Step S22: A model of the x-ray imaging system is provided. Preferably, a pre-calibrated model of the x-ray imaging system, including but not limited to a model for the source spectrum and a detector sensitivity function, is loaded into the data processing device from a storage medium.

Step S23: A set of at least two basis functions, of which at least one is designed to model the NLPV effect, is provided; e.g. loaded into the data processing device from a storage medium.

Step S24: For each basis function, a basis map of traversed thickness is estimated. For example, for each detector element and each measurement, the data processing device estimates the traversed thickness of each basis function in the set loaded in S23 from the counts registered in S21 and the detector model loaded in S22.

Step S25: Tomographic basis images are reconstructed from some of the basis thickness maps estimated in S24, including at least one basis representing the NLPV effect.

For a better understanding of the various aspects of the proposed technology, a wide variety of different non-limiting examples will now be described, including, but not limited to:

how an NLPV basis function may be constructed for use with the proposed method,
how the method may be used to create an NLPV image enabling identification of interfaces,
how the method may be used to reduce the level of NLPV artifacts in an image and
how the method may be used to find the position of an interface with high precision.

In accordance with a particular example embodiment, a number (one or more) of basis functions may be selected, such that linear combinations of these basis functions can be expected to give the linear attenuation coefficient(s) of homogeneous regions in the image volume. These will be referred to as "ordinary basis functions". They can either be measured in calibration measurements or obtained from existing x-ray attenuation coefficient databases.

In addition to the ordinary basis functions, at least one basis function is selected, which describes the effective linear attenuation coefficient of a volume element covering an interface between two materials described by some of the ordinary basis functions or linear combinations thereof. Such a basis function will be referred to as an NLPV basis function. For simplicity the following description will build upon the non-limiting assumption that only one such function is used. In one embodiment of the invention, this basis function is calculated from the ordinary basis functions by using Eq. 6, for some choice of the spatial distributions of the ordinary basis functions. The spatial average over the detector element is approximated by the average over a number of discrete, parallel projection rays as shown in FIG. 3A.

Alternatively, a more accurate model may be used, where both the source and the detector element are represented by a number of discrete points, and the average is taken over all possible projection lines from one of the source points to one of the detector points, as shown in FIG. 3B.

Alternatively, one or more NLPV basis functions may be computed from phantom measurements on interfaces between different materials. For example, consider a projection x-ray measurement with a beam parallel to an interface and situated just at the interface. If the number of photons $N_0(E)$ incident on the object is known for each energy E and the number of transmitted photons N(E) is measured using a detector with high energy resolution, an NLPV basis function can be defined as $$f_{NLPV}(E) = p - \sum_{j=1}^{N} \bar{A}_j f_j(E) \qquad \text{Eq. 9}$$

where the material composition on each side of the interface and thereby also the average basis coefficient line integrals $\bar{A}_j$ are assumed to be known.

The ordinary and NLPV basis functions are made available to the computer, by providing a method for calculating them or by storing them in a storage memory. The identification of interfaces is then accomplished by determining the expected counts in each energy bin as a function of the line integrals along the projection ray of the ordinary and NLPV basis coefficients (Eq. 8) and estimating these basis coefficient line integrals from the measured counts, e.g. by a statistical method. As an example, this statistical method may be the maximum likelihood method:

$$\hat{A}_1, \ldots, \hat{A}_N, \hat{A}_{NLPV} = \underset{A_1, \ldots, A_N, A_{NLPV}}{\operatorname{argmin}} \qquad \text{Eq. 10}$$

$$\sum_{i=1}^{M_b} \lambda_i(A_1, \ldots, A_N, A_{NLPV}) - m_i \ln \lambda_i(A_1, \ldots, A_N, A_{NLPV})$$

where $\hat{A}_j$ denotes the estimate of basis coefficient line integral j, or the least squares method (Eq. 11):

$$\hat{A}_1, \ldots \hat{A}_N, \qquad \text{Eq. 11}$$

$$\hat{A}_{NLPV} = \underset{A_1, \ldots, A_N, A_{NLPV}}{\operatorname{argmin}} \sum_{i=1}^{M_b} (m_i - \lambda_i(A_1, \ldots, A_N, A_{NLPV}))^2$$

The result of this decomposition is a set of estimated line integrals $\hat{A}_j$ and $\hat{A}_{NLPV}$ for the projection lines from the source to every detector element. In projection x-ray imaging, the estimated NLPV basis coefficient line integrals $\hat{A}_{NLPV}$ form an NLPV basis image which can be viewed may be viewed as it is. More generally, these line integrals together form a basis image representation, by which is meant a dataset which contains the necessary information for generating a basis image by some processing such as e.g. rearrangement of the data points, re-interpolation or reconstruction. In CT imaging, the resulting basis image representation is a basis sinogram, which may be reconstructed to yield a tomographic basis image. Another example of a basis image representation is a set of basis coefficient line integrals estimated from projection data acquired with a curved detector, which requires re-interpolation to an equi-spaced rectangular grid to be viewed as an image. A basis coefficient representation can also be a set of coefficients in a series expansion of the basis image as linear combination of some sort of spatial basis functions, such as sinusoidal functions or orthogonal polynomials.

In all these cases regions with interfaces parallel to the beam direction can be identified as regions with high signal intensity in the resulting NLPV basis image, in contrast to gradual transitions, which have low signal intensity. The NLPV basis image may be viewed by itself or used as a color overlay to an ordinary CT image or projection image to enable identification of image regions with interfaces.

In addition to projection and computed tomography imaging, the method described here can also be used in tomosynthesis, which is an imaging modality where a tomographic image is reconstructed from projection images acquired in a limited view angle range, by performing the tomosynthesis reconstruction from an NLPV basis image.

The method can be used in any of a wide variety of hardware implementations, included but not limited to x-ray projection imaging devices, mammography devices, CT scanners, tomosynthesis systems and C-arms and other interventional x-ray devices. It can be utilized in different areas of application such as medical imaging, nondestructive testing and security scanning.

Basis material decomposition in x-ray imaging has previously been covered in patent applications WO2007034356, WO2014001984, WO2008135897, WO2008021664 and WO2013011418 and U.S. Pat. Nos. 7,778,380, 8,615,120 and 8,213,566, but none of these references describe the use of a basis function that models the nonlinear partial volume effect or which is specific to projection rays passing along interfaces.

To get a clear signal in the NLPV image without excessive dose, it is desirable to concentrate the measurement to projection lines that are parallel to the interface or interfaces to be investigated. This suggests that it may be preferable to first acquire an initial tomographic image, identify regions of the image where it is desirable to localize interfaces, and then acquire a projection or tomosynthesis image with the source and the detector in such a position that a large fraction of the projection rays can be expected to pass through any interfaces present, parallel to the interfaces. Decomposition of this projection image into a NLPV basis image allows identifying which projection rays have passed through an interface and thereby identifying the location of interfaces in the original tomographic image. For example, a computed tomography, tomosynthesis or C-arm system may be used to acquire an initial tomographic image and then put in a stationary position to acquire a projection image. This may include tilting of the gantry, if that is supported by the hardware. It may also be desirable to collimate the beam during the acquisition of the projection image in order to irradiate only the region of interest and avoid excessive dose to the patient.

Unconstrained optimization sometimes leads to a very large positive value for one basis coefficient and a very large negative value for another basis coefficient, which may be unphysical depending on the choice of basis function. It may therefore be beneficial to enforce non-negativity of some or all of the basis coefficient line integrals by using a constrained optimization algorithm to minimize the expressions in Eq. 10 and Eq. 11 in order to avoid outliers in the estimated basis coefficient line integrals, which can cause streak artifacts in the reconstructed CT images.

In order for the reconstructed NLPV basis image to be an accurate representation of the regions with interfaces in the image, the estimated NLPV component should ideally be proportional to the path length of the interface that the ray in question has passed through. However, this condition might not be fulfilled when $A_{NLPV}$ is estimated with the above method. Therefore, the estimated NLPV component may be corrected by a formula or look-up table to the path lengths that have been found in advance by simulations or measurements. Such a correction may take the estimated NLPV basis coefficient line integral as input:

$$\hat{A}_{NLPV}^{corr} = f(\hat{A}_{NLPV}) \quad \text{Eq. 12}$$

or take all or a subset of the estimated basis coefficient line integrals as inputs:

$$\hat{A}_{NLPV}^{corr} = f(\hat{A}_1, \ldots, \hat{A}_N, \hat{A}_{NLPV}) \quad \text{Eq. 13}$$

As an example, this can be done by constructing the NLPV basis function from a measurement on a sharp interface between two materials. By keeping the area fraction which is occupied by each material constant but varying the common thickness t in the ray direction of these materials, as measured in some unit system, the expected number of photon counts and thereby the basis coefficient line integrals $\hat{A}_{NLPV}$ resulting after basis material decomposition can be calculated or simulated. Eq. 12 can then be implemented by interpolation between the data points $(\hat{A}_{NLPV}^{corr})$, so that $\hat{A}_{NLPV}$ is mapped to a t value which is taken to be the corrected basis coefficient line integral $\hat{A}_{NLPV}^{corr}$. Alternatively such a simulation or measurement may be done for several different cross-section area fractions of the constituent materials and an analytic function, such as a polynomial, fitted to the data points, e.g. by least squares fitting:

$$\hat{A}_j = p_j(t), j=1, \ldots, N$$

$$\hat{A}_{NLPV} = p_{NLPV}(t) \quad \text{Eq. 14}$$

whereupon Eq. 13 may be implemented, e.g. by least squares fitting:

$$\hat{A}_{NLPV}^{corr} = \operatorname*{argmin}_t \left( \sum_{j=1}^{N} (p_j(t) - \hat{A}_j)^2 + (p_{NLPV}(t) - \hat{A}_{NLPV})^2 \right) \quad \text{Eq. 15}$$

In another embodiment of the invention, the identification of interfaces is carried out after reconstruction of tomographic images for each energy bin, in a way similar to that described in Firsching et al., "Quantitative material reconstruction in CT with spectroscopic x-ray pixel detectors—a simulation study", Nuclear Science Symposium Conference Record 4, 2257-2259 (October 2006), with the difference that a NLPV basis function is included in the decomposition here. To this end, a set of ordinary basis functions are selected by measuring the reconstructed attenuation coefficient in every energy bin in homogeneous regions in the image consisting of each basis material. Furthermore, an NLPV basis function is selected by measuring the reconstructed attenuation coefficient in every energy bin at an interface between two different materials. Letting $$M = \begin{pmatrix} \mu_{11} & \cdots & \mu_{1N} & \mu_{1,NLPV} \\ \vdots & \ddots & \vdots & \vdots \\ \mu_{M_b 1} & \cdots & \mu_{M_b N} & \mu_{M_b NLPV} \end{pmatrix} \quad \text{Eq. 16}$$

where $\mu_{ij}$ is the reconstructed attenuation coefficient in bin i, for basis material j. The basis coefficients $a_i$ can be found for each voxel in the image volume by least squares fitting of the measured attenuation coefficients $\mu = (\mu_1, \ldots, \mu_{M_b})^t$ (where t denotes transpose) to these basis functions:

$$\hat{a} = (M^t M)^{-1} M^t \mu \quad \text{Eq. 17}$$

In another embodiment of the invention, the basis coefficient line integrals $A_i$ are computed by constrained optimization, where one or more linear or nonlinear constraints are imposed on the set of basis coefficient line integrals. For example, the basis coefficient line integrals corresponding to two of the ordinary basis functions may be constrained to sum to a known total path length that the ray has gone through the object. This total path length may be measured separately by mechanical means, such as with a compression plate, or measured from projection data acquired in other view angles, in the case of computed tomography.

The functional form of the forward model (Eq. 8) and the NLPV basis function (Eq. 6) can be varied. By exchanging the NLPV basis function (Eq. 6) for $$\tilde{f}_{NLPV}(E) = \exp\left(\sum_{j=1}^{N} \overline{A}_j f_j(E)\right) \overline{\exp\left(-\sum_{J=1}^{N} A_J(x,y) f_J(E)\right)} - 1 \quad \text{Eq. 18}$$

Eq. 7 can be rewritten as:

$$\lambda_i = \int_{E=0}^{\infty} S_i(E) \exp\left(-\sum_{j=1}^{N} \overline{A}_j f_j(E)\right)\left(1 + \tilde{f}_{NLPV}(E)\right) dE \quad \text{Eq. 19}$$

which suggests that basis material decomposition can be made with the forward model:

$$\lambda_i = \int_{E=0}^{\infty} S_i(E) \exp\left(-\sum_{j=1}^{N} A_j f_j(E)\right)\left(1 + A_{NLPV} \tilde{f}_{NLPV}(E)\right) dE \quad \text{Eq. 20}$$

instead of Eq. 8.

A further possible modification of Eq. 20 is to let the NLPV basis coefficient line integral be quadratic in the forward model:

$$\lambda_i = \int_{E=0}^{\infty} S_i(E) \exp\left(-\sum_{j=1}^{N} A_j f_j(E)\right)\left(1 + A_{NLPV}^2 \tilde{f}_{NLPV}(E)\right) dE \quad \text{Eq. 21}$$

This formula can be motivated by Taylor expanding the NLPV basis function of Eq. 18:

$$\tilde{f}_{NLPV}(E) \approx \frac{1}{D} \int\int \exp\left(-\sum_{j=1}^{N}(A_j - \overline{A}_j)f_j(E)\right) dxdy - 1 =$$

$$\frac{1}{D}\int\int 1 - \sum_{j=1}^{N}(A_j - \overline{A}_j)f_j(E) + \quad \text{Eq. 22}$$

$$\left(\sum_{j=1}^{N}(A_j - \tilde{A}_j)f_j(E)\right)^2 dxdy - 1 = \overline{\left(\sum_{J=1}^{N}(A_J - \overline{A}_J)f_J(E)\right)^2}$$

Here, the integral is taken over the detector surface. Since the linear term vanishes, $\tilde{f}_{NLPV}$ is proportional to the square of the deviation from $\overline{A}_j$, which suggests Eq. 22.

In another embodiment of the invention, CT image reconstruction and basis material decomposition may be carried out simultaneously by letting the ordinary and NLPV basis coefficients $a_l$ and $a_{NLPV}$ in every voxel in the image volume be the unknown parameters and estimating these from the measurements in all energy bins for all projection lines by a statistical estimation method, such as maximum a posteriori:

$$\hat{\alpha} = \underset{\alpha}{\mathrm{argmin}} \sum_{i=1}^{M_b} \sum_{k=1}^{M_d} (\lambda_{ik}(a) - m_{ik}\lambda_{ik}(a)) + \quad \text{Eq. 23}$$

$$\sum_{l=1}^{M_v} \sum_{l'=1}^{M_v} \left(\sum_{j=1}^{N} c_{ll'} g(a_{jl} - a_{jl'}) + c_{ll'} g(a_{NLPV,l} - a_{NLPV,l'})\right)$$

Here, $a_{jl}$ is the basis coefficient of material j in detector element l, $a_{NLPV,l}$ is the NLPV basis coefficient in detector element l and a is a vector containing $a_{jl}$ for j=1, ..., N as well as $a_{NLPV,l}$ for l=1, ..., $M_v$ where $M_v$ is the number of voxels in the image volume. $\lambda_{ik}(a)$ and $m_{ik}$ is the expected and registered counts, respectively, in bin i and detector element k. $\lambda_{ik}(a)$ is given by Eq. 8 with $\lambda_j$ and $A_{NLPV}$ substituted for $A_{jk}$ and $A_{NLPV,k}$ which are the line integrals of the ordinary and NLPV basis functions along the line from the source to detector element k.

$$c_{ll'} = \begin{cases} 1/d_{ll'} & \text{if voxels } l \text{ and } l' \text{ are neighbors} \\ 0 & \text{otherwise} \end{cases} \quad \text{Eq. 24}$$

where $d_{ll'}$ is the center-to-center distance between voxels l and l'. Two voxels are regarded to be nearest neighbors if they have at least one common corner, edge or side. $g(\Delta)$ is a function of the basis coefficient difference which controls how variations between neighboring voxels should be penalized. It may be a quadratic function or an edge-preserving penalty function such as the Huber penalty:

$$g(\Delta) = \begin{cases} \Delta^2/2 & |\Delta| \leq \delta \\ \delta|\Delta| - \delta^2/2 & |\Delta| \geq \delta \end{cases} \quad \text{Eq. 25}$$

The minimization may be carried out by e.g. iterative coordinate descent or by using surrogate functions like the method described in Fessler et al., Maximum-likelihood dual-energy tomographic image reconstruction, Proceedings of SPIE Vol. 4684 (Medical imaging 2002: Image processing), pp 38-49, where a similar reconstruction problem is formulated, although without any basis function representing the NLPV term.

The function that is minimized in Eq. 23 is called a penalized data discrepancy. The first term is the data discrepancy, or the data error, resulting from a specific value of a, while the second term is a penalty term, or regularization term, which controls the texture of the resulting image, e.g. by penalizing large variations between neighboring voxels. Both terms may take other forms than those presented in Eq. 23: for example the data discrepancy term can be replaced by a mean square error, and the penalty term may include voxels located further apart than nearest neighbors, or $g(\Delta)$ may be a the absolute value of $\Delta$ or a quadratic function of $\Delta$.

As demonstrated by the above examples, the invention may include expressing either the linear attenuation coefficient(s) or line integrals thereof as a combination of basis functions. In a sense, the invention can be regarded as using a combination of basis functions, including at least one NLPV basis function, to express a representation of the linear attenuation coefficient(s), by which is typically meant a dataset containing the necessary information for generating a map, or image representation, of the linear attenuation coefficient(s) by some processing, e.g. based on rearrangement of the data points, re-interpolation or reconstruction. A representation can be line integrals of the linear attenuation coefficient or a set of coefficients in a series expansion of the linear attenuation coefficient as linear combination of some sort of spatial basis functions, such as sinusoidal functions or orthogonal polynomials.

Similarly, the energy-resolved image data that is used as input to the decomposition does not have to be the number of photons in each energy bin and detector element, but can be a representation of the number of photons, by which is meant a quantity which is related to the number of photons and can be used to extract information about the number of photons and possibly also their spectral distribution. An example is the negative logarithm of the fraction of transmitted and incident photons. Another example is the signal in an energy integrating detector, where the contribution of each photon is weighted by its energy.

The more basis functions are included in the decomposition, the more noisy their estimates will be. However, in some cases it is known beforehand in which region or regions of the image that it is of interest to locate interfaces. If the number of basis functions necessary to represent the substances in these regions is smaller than the number of basis functions needed for the entire volume, the following method can be used to reduce noise in the basis images:

A first material decomposition is made using all the basis functions needed to represent the substances in the image volume, but without the NLPV basis. Basis images are reconstructed from the decomposed sinograms, and a region of interest (ROI) where interfaces should be identified is selected, manually or by a computer algorithm. Then each basis image is multiplied with a mask taking the value 0 inside the region of interest and 1 everywhere else and forward projected, resulting in a set of sinograms containing the basis coefficient line integrals of the part of the image volume that is outside the ROI. Denote these exterior basis coefficient line integrals by $A_j^e$. Then, a second basis material decomposition is performed using the modified forward model:

$$\lambda_i = \int_{E=0}^{\infty} S_i(E) \exp\left(-\sum_{j \in B} A_j f_j(E) - \sum_{j \in \{1,\ldots,N\} \backslash B} A_j^e f_j(E) - A_{NLPV} f_{NLPV}(E)\right) dE \quad \text{Eq. 26}$$

where B denotes the set of basis indices that are expected to be present in the ROI. The unknown variables to be estimated here are $A_j$ for $j \in B$ and $A_{NLPV}$. The basis coefficient line integral sinograms estimated in the second basis material decomposition step together with the sinograms estimated in the first step for $j \in \{1, \ldots, N\} \backslash B$ form a complete set of sinograms that can be reconstructed to give a set of basis images.

Another way of obtaining an NLPV basis image is to identify the ROI in a preliminary reconstructed image as above and reconstruct the image iteratively according to Eq. 23 but with a constrained optimization algorithm that forces $a_{jl}$ to be 0 for pixels l in the ROI and $j \in \{1, \ldots, N\} \backslash B$.

In another embodiment of the invention, more than one NLPV basis function may be estimated in the basis material decomposition step, i.e. by replacing (Eq. 8) by:

$$\lambda_i = \int_{E=0}^{\infty} S_i(E) \exp\left(-\sum_{j=1}^{N} A_j f_j(E) - \sum_{k=1}^{N_{NLPV}} A_{NLPV,k} f_{NLPV,k}(E)\right) dE \quad \text{Eq. 27}$$

where $N_{NLPV}$ is the number of NLPV basis functions. These NLPV basis functions may be obtained by measurement on or simulation of interfaces between different material combinations or different basis functions. Different types of interfaces, i.e. with different material combinations on each side of the interface, can then be expected to show up more strongly in some of the resulting NLPV basis images than in the others. The reconstructed NLPV basis images may be viewed separately or summed together to make a common image where any kinds of interfaces can be seen.

In previous work, dual energy CT has been used to separate partial volume regions of air and contrast-tagged colon content from soft tissue in the colon wall (Carmi et al., A Unique Noncathartic CT Colonography Approach by Using Two-Layer Dual-Energy MDCT and a Special Algorithmic Colon Cleansing Method, 2008 IEEE Nuclear Science Symposium Conference Record, M10-132 and Cai et al., "Low-dose dual-energy electronic cleansing for fecal-tagging CT colonography", Proceedings of SPIE, Vol. 8670, 86700W-1. However, the methods presented in these publications are not specifically aimed at detecting interfaces and do not build on basis material decomposition with a specific basis for the nonlinear partial volume effect. Neither are they based upon the fact that the nonlinear partial volume effect gives rise to energy responses which do not appear in the constituent materials themselves.

In another aspect of the invention, the estimated ordinary and NLPV basis functions may be used to generate an image where NLPV artifacts are corrected for.

One way of correcting for NLPV artifacts that has been described previously is by estimating the gradient of the linear attenuation coefficient(s) from the image pixels surrounding the region that should be corrected, and using this information to correct for the nonlinear partial volume effect as described in U.S. Pat. No. 7,551,710 and U.S. Pat. No. 5,727,041. A related method is to divide volume averaged image pixels into sub-pixels which are assumed to contain specified materials, e.g. bone and soft tissue, depending on the attenuation in adjacent pixels.

Another technique is to assume that the shape of the object causing the artifacts is known a priori and to fit the location of this object iteratively to data, as described in "Overcoming Nonlinear Partial Volume Effects in Known-Component Reconstruction of Cochlear Implants" J. W. Stayman et al., SPIE Medical imaging 2013, Vol. 8668, 86681L A method for reducing partial volume artifacts using dual energy CT has previously been published (Xue et al. "A correction method for dual energy liquid CT image reconstruction with metallic containers", Journal of X-Ray Science and Technology 20 (2012), 301-316). However, the method presented in that work requires prior knowledge of the shape of the metal container, and it does not include any basis function modelling the partial volume effect specifically in the basis material decomposition.

However, there is an ongoing need for more effective suppression of partial volume artifacts. The following describes such a method which builds upon the above described method for identifying interfaces.

In the notation employed here, it is the averaged ordinary basis coefficient line integrals $\overline{A}_i$ which are sought, since these form basis sinograms which are the result of a convolution of the original sinograms with a blurring kernel. When reconstructed, these yield basis images which are linear convolutions of the true basis images with a blurring kernel, meaning that there are no artifacts stemming from the nonlinearity of the partial volume effect in such an image.

According to Eq. 7, when basis material decomposition is carried out on a projection line that has passed exactly the material distribution that was used to define the NLPV basis (Eq. 6), the resulting ordinary basis coefficient line integrals $A_i$ will be equal to the true averaged basis coefficient line integrals $\overline{A}_i$ (at least to the extent that the statistical estimator used is approximately unbiased). This can be expected to be approximately true also for other material combinations. Therefore, NLPV-artifact-reduced images may be obtained by estimating ordinary and NLPV basis functions as described above and reconstructing ordinary basis images from the estimated sinograms of ordinary basis coefficient line integrals. These images can be displayed without further processing, or a linear combination of them may be formed and displayed, e.g. to optimize the CNR of some feature or to create a synthetic monoenergetic image.

The above method does not remove the NLPV artifacts totally, however, since the forward model Eq. 8 is only exact for one particular combination of spatially variant basis coefficient line integrals. Therefore a correction step may be added after the basis material decomposition, with the estimated ordinary and NLPV basis coefficient line integrals as inputs, in order to better estimate the actual values of $\bar{A}_1 \ldots \bar{A}_N$:

$$(\hat{A}_1^{corr}, \ldots, \hat{A}_N^{corr}) = f(\hat{A}_1, \ldots, \hat{A}_N, \hat{A}_{NLPV}) \quad \text{Eq. 28}$$

In practice this may be implemented as a lookup table or a functional mapping, in a similar way as described above for correction of the NLPV components: If Eq. 3, Eq. 8 and Eq. 10 are used to simulate forward projection and basis material decomposition for a number of different basis coefficient line integral distributions $A_1(x,y), \ldots A_N(x,y)$ over the detector area with averages $\bar{A}_1, \ldots, \bar{A}_N$ a number of functions, e.g. polynomials or spline interpolants, may be fitted to the data points $(\hat{A}_1, \ldots, \bar{A}_N; \hat{A}_1, \ldots, \hat{A}_N, \hat{A}_{NLPV})$ e.g. by least squares fitting:

$$\hat{A}_j = p_j(\bar{A}_1, \ldots, \bar{A}_N), j=1, \ldots, N$$

$$\hat{A}_{NLPV} = p_j(\bar{A}_1, \ldots, \bar{A}_N) \quad \text{Eq. 29}$$

and then Eq. 28 can be implemented as, for example, a least squares fitting of the estimated basis coefficient line integrals to the value set of the range of the interpolating functions:

$$(\hat{A}_N^{corr}, \ldots, \hat{A}_N^{corr}) = \underset{\bar{A}_1, \ldots, \bar{A}_N}{\operatorname{argmin}} \left( \sum_{j=1}^{N} \left(p_j(\bar{A}_1, \ldots, \bar{A}_N) - \hat{A}_j\right)^2 + \left(p_{NLPV}(\bar{A}_1, \ldots, \bar{A}_N) - \hat{A}_{NLPV}\right)^2 \right) \quad \text{Eq. 30}$$

As an alternative, the estimation could be made using the maximum likelihood method, assuming that $p_j(\bar{A}_1, \ldots, \bar{A}_N) - \hat{A}_j$ and $p_{NLPV}(\bar{A}_1, \ldots, \bar{A}_N) - \hat{A}_{NLPV}$ are random variable with some specified probability distributions, e.g. normal or lognormal distributions.

Figure 10:
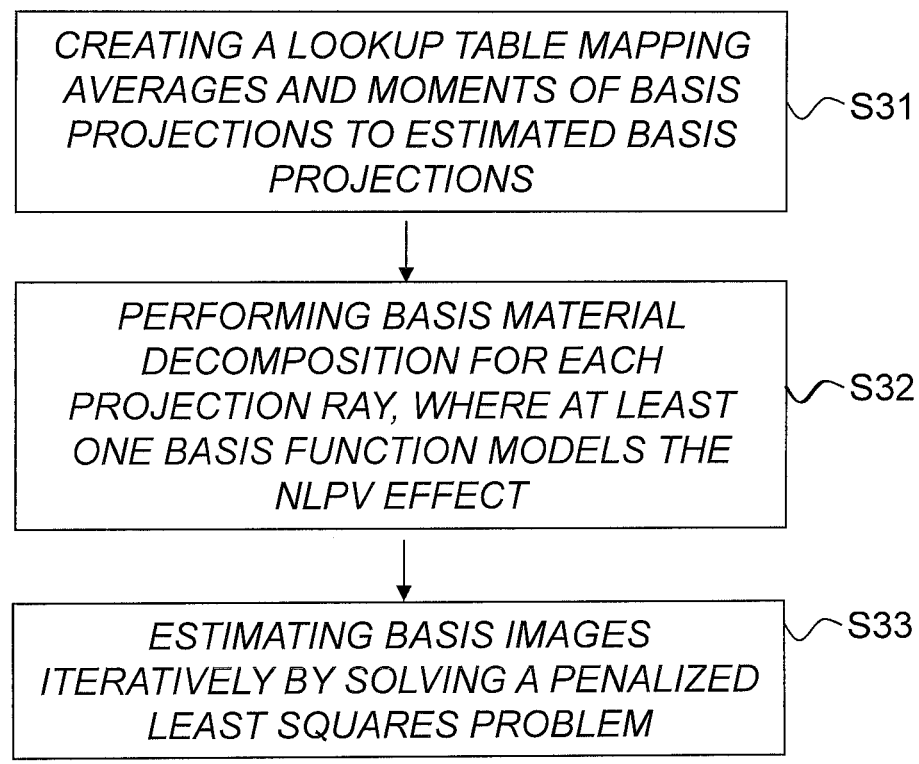
FIG. 10 is a schematic flow diagram illustrating an example of an algorithm for finding the position of an interface with high precision.
Figure 12:
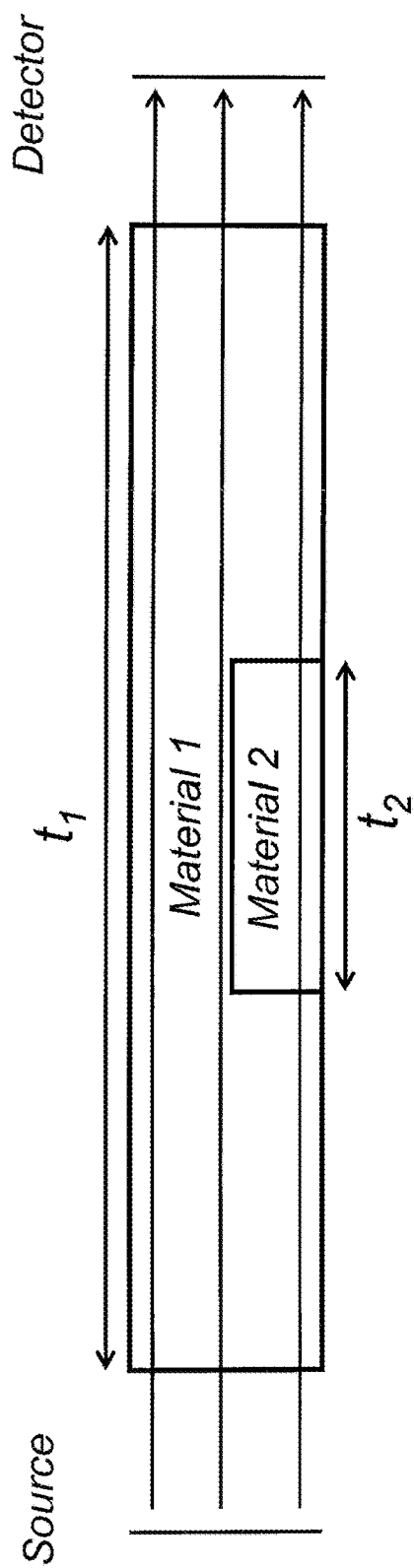
FIG. 12 is a schematic diagram showing an example of the geometry for simulating averages and first moments of basis coefficient line integrals for a beam passing a thickness t1 of material 1 with a partially intruding insert of thickness t2 of a second material.

In another aspect of the invention, a method is provided for finding the position of an interface with high precision, as illustrated in FIG. 10. For example, it may be important to measure the size of a blood vessel, or locating the boundary of a calcified plaque. In these situations, it is often known or at least assumed that there is a sharp interface between two materials, but the exact position of the interface is uncertain because of the finite image resolution which in turn is caused by the finite detector width. The following example method allows finding the boundaries of an object with higher precision than what would be possible without energy information:

Step S31: The first step is to create a lookup table which maps the basis coefficient line integral distributions $A_1(x,y), \ldots, A_N(x,y)$ to estimated basis coefficient line integrals $\hat{A}_1, \ldots, \hat{A}_N, \hat{A}_{NLPV}$. This is accomplished by simulating the transmission through a number of different basis coefficient line integral distributions $A_1(x,y), \ldots, A_N(x,y)$ over the detector area with averages $\bar{A}_1 \ldots \bar{A}_N$, using Eq. 3, Eq. 8 and Eq. 10 to simulate forward projection and basis material decomposition. The different basis coefficient line integral distributions may for example be obtained from different thicknesses $t_1$ of a first material, modelling a background tissue type, in which a second material intrudes partially, covering different fractions $\beta$ of the beam cross-section and extending different distances $t_2$ in the beam direction, as shown in FIG. 12. This may be made for a pair of materials likely to be present in the region where it desired to find the position of an interface, or for several different material pairs. A thickness $t_3$ of a third material, homogeneous across the beam cross-section, may optionally be added.

In practice the lookup table may be indexed by the averaged projections $\bar{A}_1 \ldots \bar{A}_N$ together with the first central moments $A_1^{M01}, \ldots, A_N^{M01}$ and $A_1^{M10}, \ldots, A_N^{M10}$ where:

$$A_i^{M10} = \int (x-x_c) A_i(x,y) dx dy$$

$$A_i^{M01} = \int (y-y_c) A_i(x,y) dx dy \quad \text{Eq. 31}$$

and the basis coefficient line integral distributions $A_1(x,y), \ldots, A_N(x,y)$ are mapped to estimated basis coefficient line integrals by calculating their averages and first moments and interpolating between the points in the table, yielding:

$$(\hat{A}_1, \ldots, \hat{A}_N, \hat{A}_{NLPV}) = f(\bar{A}_1, \ldots, \bar{A}_N, A_1^{M01}, \ldots, A_N^{M01}, A_1^{M10}, \ldots, A_N^{M10}) \quad \text{Eq. 32}$$

Alternatively, a polynomial or another analytical function may be fitted to the data points.

Step S32: The second step is to acquire an image using an energy-resolving detector and carrying out basis material decomposition with the same set of basis functions as that used when creating the lookup table, including the NLPV basis function. The result is a set of ordinary and NLPV basis coefficient line integral sinograms.

Step S33: The third step is to estimate the basis images $a_1, \ldots, a_N$ iteratively from the decomposed basis coefficient line integrals. To this end, the image volume is discretized and each the beam from the source to each detector element is approximated by a number of subrays from different points on the source to different points on the detector element. The images are preferably estimated by solving a penalized mean square error problem iteratively:

$$\hat{\alpha} = \underset{\alpha}{\operatorname{argmin}} \sum_{k=1}^{M_d} \left(\hat{A}_k - A_k^{sim}\right)^t C^{-1} \left(\hat{A}_k - A_k^{sim}\right) + \sum_{l=1}^{M_v} \sum_{l'=1}^{M_v} \left( \sum_{j=1}^{N} c_{ll'} g(a_{jl} - a_{jl'}) + c_{ll'} g(a_{NLPV,l} - a_{NLPV,l'}) \right) \quad \text{Eq. 33}$$

where $A_k^{sim} = f(\bar{A}_{1,k}, \ldots, \bar{A}_{N,k}, A_{1,k}^{M01}, \ldots, A_{N,k}^{M01}, A_{1,k}^{M10}, \ldots, A_{N,k}^{M10})$ is a vector of simulated basis coefficient line integral averages and first moments obtained from the line integrals of $a_1, \ldots, a_N$ along the different subrays from the source to detector element k, i.e. from discrete estimates of $A_1(x,y), \ldots, A_N(x,y)$. C is the covariance matrix of the basis coefficient line integral estimates $\hat{A}$. It will typically vary from projection ray to projection ray and can be estimated from the Cramer-Rao Lower bound (Schirra et al. "Statistical Reconstruction of Material Decomposed Data in Spectral CT", IEEE Transactions on Medical Imaging 32, no. 7, July 2013, 1249-1257) or as the empirical covariance calculated over homogeneous regions in the sinogram data. $M_d$ is the number of detector elements, $M_v$ is the number of voxels and $c_{ij'}$ and g are given by Eq. 24 and Eq. 25. Minimization of Eq. 33 is done using an iterative optimization method, for example iterative coordinate descent or conjugate gradient.

The input to the mapping constructed in the first step above does not have to include first moments but can in general be a representation of the spatially variant basis coefficient line integrals $A_1(x,y), \ldots, A_N(x,y)$, by which is meant a collection of data which allows inferring information about the spatial distribution of the basis coefficient line integrals. This representation could be a set of basis coefficient line integrals along selected subrays, or a set of coefficients in a series expansion of the spatial distribution of a basis coefficient line integral as linear combination of some sort of spatial basis functions, such as sinusoidal functions or orthogonal polynomials.

In a similar way as for Eq. 23, the form of Eq. 33 can be varied. For example, the data discrepancy term can be replaced by a negative log likelihood function, assuming some statistical distribution of $\hat{A}_k - A_k^{sim}$ such as multivariate normal or lognormal. Also, the penalty term may include voxels located further apart than nearest neighbors, or $g(\Delta)$ may be a the absolute value of $\Delta$ or a quadratic function of $\Delta$.

Figure 13:
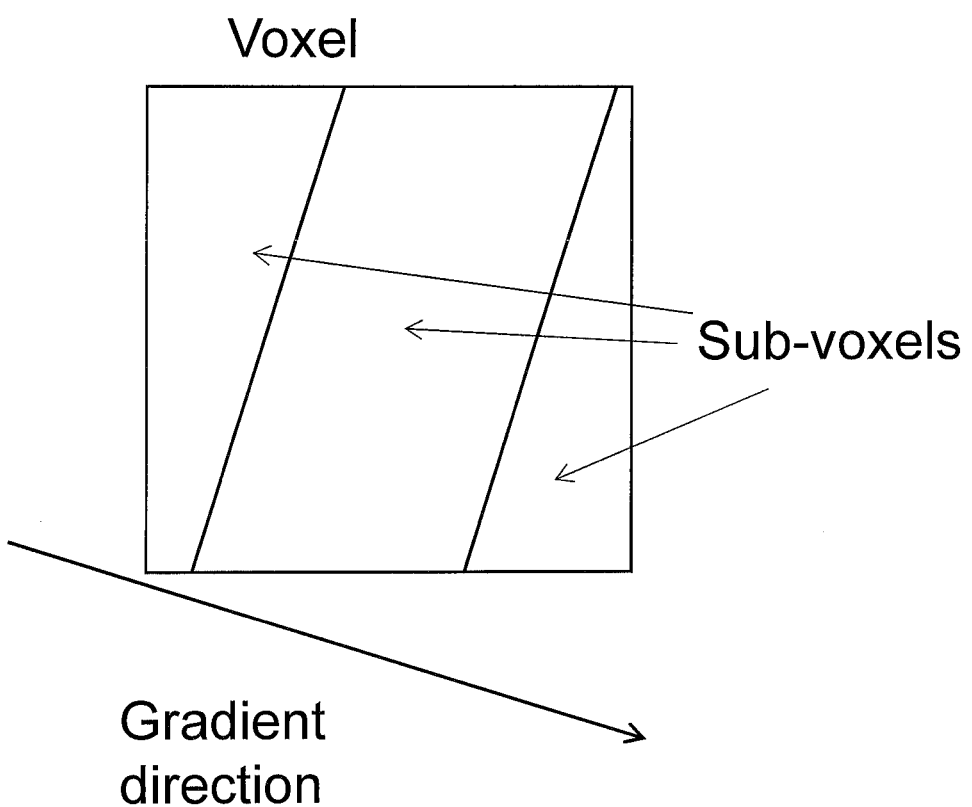
FIG. 13 is a schematic diagram showing an example of how a voxel may be subdivided into sub-voxels, by introducing one or more borders orthogonal to the image gradient direction.

It is desirable to do this iterative reconstruction on a voxel grid which is finer than the ones typically used for the same source and detector element size, since this method uses the information in the NLPV basis coefficient line integrals to improve spatial resolution. One way of constructing a finer grid is by simply subdividing each voxel into subvoxels using a cartesian grid. Since a very fine voxel grid may cause image reconstruction to become prohibitively time-consuming, it may be desirable to restrict this subsampling to an ROI consisting of the immediate surroundings of the interface that is to be located, which can be identified by first reconstructing a normal CT image from the data. Another method of refining the voxel grid is by using such a preliminary image to calculate the image gradient at the position of the interface which is to be located and subdividing each of the voxels in the vicinity of the interface in the gradient direction into two or more slices, as shown in FIG. 13. To reduce noise one may optionally choose to apply a spatial low-pass filter to the image before computing the image gradient. As an alternative, if the ROI contains an object which can be well approximated by a geometric shape, like a cylinder may approximate a portion of a blood vessel, the gradient may be replaced by a surface normal of that geometric shape, once the position, size and orientation of the shape has been found by fitting it to the image data.

There are possible modifications to the third step. Assume that the interface transition is sharp, not gradual, and that the material compositions on each side of the interface are known beforehand, or can be inferred from a first reconstruction of basis material images resulting from ordinary basis decomposition without NLPV basis. Then the ROI around the interface can be assumed to be binary, meaning that the voxels there can assume only one of two possible sets of basis coefficient values, the object composition $(a_1^o, \ldots, a_N^o)$ and the background composition $(a_1^b, \ldots, a_M^b)$. Eq. 33 is then modified such that voxels within the ROI are restricted to these to values whereas other voxels are free to assume any basis coefficient values.

Furthermore, if the voxels situated on the interface are subdivided into two slices in the gradient direction as described above, it is possible to let the position of the border between the subvoxels be the free parameter that is optimized over in the reconstruction, under the assumption that the subvoxel before the interface consists of the less attenuating of the two materials while the subvoxel after the interface consists of the more attenuating one, where "before" and "after" relate to the order in which these subvoxels are traversed when moving in the gradient direction.

The third step of the method described here is similar to the one described in Schirra et al. "Statistical Reconstruction of Material Decomposed Data in Spectral CT", IEEE Transactions on Medical Imaging 32, no. 7, July 2013, 1249-1257, although no NLPV basis and no lookup table mapping basis coefficient line integral distributions to estimated basis coefficient line integrals were used in that publication.

It will be appreciated that the methods and devices described herein can be combined and re-arranged in a variety of ways.

For example, embodiments may be implemented in hardware, or in software for execution by suitable processing circuitry, or a combination thereof.

The steps, functions, procedures, modules and/or blocks described herein may be implemented in hardware using any conventional technology, such as discrete circuit or integrated circuit technology, including both general-purpose electronic circuitry and application-specific circuitry.

Particular examples include one or more suitably configured digital signal processors and other known electronic circuits, e.g. discrete logic gates interconnected to perform a specialized function, or Application Specific Integrated Circuits (ASICs).

Alternatively, at least some of the steps, functions, procedures, modules and/or blocks described herein may be implemented in software such as a computer program for execution by suitable processing circuitry such as one or more processors or processing units.

The flow diagram or diagrams presented herein may therefore be regarded as a computer flow diagram or diagrams, when performed by one or more processors. A corresponding apparatus may be defined as a group of function modules, where each step performed by the processor corresponds to a function module. In this case, the function modules are implemented as a computer program running on the processor.

Examples of processing circuitry includes, but is not limited to, one or more microprocessors, one or more Digital Signal Processors, DSPs, one or more Central Processing Units, CPUs, video acceleration hardware, and/or any suitable programmable logic circuitry such as one or more Field Programmable Gate Arrays, FPGAs, or one or more Programmable Logic Controllers, PLCs.

It should also be understood that it may be possible to re-use the general processing capabilities of any conventional device or unit in which the proposed technology is implemented. It may also be possible to re-use existing software, e.g. by reprogramming of the existing software or by adding new software components.

There is provided a system for processing a radiographic image acquired with at least two energy levels. The system is configured to obtain energy-resolved image data representative of the radiographic image with at least two energy levels. The system is also configured to perform basis decomposition of the image data into at least one basis image representation, based on a model where a combination of at least two basis functions is used to express a representation of at least one linear attenuation coefficient, where at least one basis function, also referred to as an ordinary basis function, models a physical material and at least one other basis function, also referred to as an NLPV basis function, models the Non-Linear Partial Volume, NLPV, effect.

In a specific example, the system is configured to obtain energy-resolved image data including a representation of the number of photons incident per detector element. The system is also configured to perform the basis decomposition based on a model that defines the number of photons incident per detector element as a function of i) basis coefficients used to express the linear attenuation coefficient(s) or line integrals of the basis coefficients, and ii) the at least two basis functions. The system is further configured to estimate at least a subset of the basis coefficients or at least a subset of the line integrals of the basis coefficients to provide a representation of the basis image(s).

By way of example, the system may be configured to receive image data of an energy-resolved sinogram as input, and configured to produce at least one basis image corresponding to an NLPV basis function, also referred to as an NLPV basis image, or at least one subsequently reconstructed tomographic NLPV basis image, enabling the identification of interfaces.

In a particular example, the system is configured to apply a mapping to at least one of the NLPV basis images resulting from the decomposition, resulting in a NLPV basis image approximately proportional to the traversed common path length of an interface.

For example, the system may be configured to operate based on an energy-resolved sinogram as input and where initially a first basis material decomposition is made using a model without NLPV basis, resulting in a set of at least one basis image which is reconstructed to yield at least one tomographic basis image, which is replaced by zero in at least a subset of the image volume and forward projected to yield at least one sinogram of basis line integrals, and where subsequently a second decomposition is made using a model including at least one ordinary basis function and at least one NLPV basis function, where the line integrals of the model corresponding to at least one ordinary basis function are assumed to be equal to said sinogram of line integrals.

In another example, the system is configured to receive image data of an energy-resolved sinogram as input, and configured to produce at least one basis image corresponding to an ordinary basis function, also referred to as an ordinary basis image which is subsequently reconstructed to yield at least one tomographic ordinary basis image.

Preferably, the at least one tomographic ordinary basis image has a reduced level of NLPV artifacts compared to a tomographic basis image reconstructed from a basis image resulting from a basis material decomposition without NLPV basis.

By way of example, the system may be configured to apply a mapping to at least one of the ordinary basis images resulting from the decomposition, before said basis image is reconstructed, resulting in at least one corrected ordinary basis image.

In yet another example, the system is configured to output basis image representation(s) including at least one sinogram of ordinary basis coefficient line integrals and at least one sinogram of NLPV basis coefficient line integrals, and to subsequently compute a set of ordinary tomographic basis images corresponding to ordinary basis functions by minimizing a penalized data discrepancy between said at least one sinogram of ordinary basis coefficient line integrals and said at least one sinogram of NLPV basis coefficient line integrals, on one side, and at least one sinogram of simulated ordinary basis coefficient line integrals obtained from a forward projection of said tomographic basis images, on the other side, and where said forward projection is calculated with at least two line integrals from the source to each detector element, yielding a spatially variant basis coefficient line integral for each detector element, and where a mapping is used to translate a representation of said spatially variant basis coefficient line integrals into said at least one sinogram of simulated ordinary basis coefficient line integrals and said at least one sinogram of NLPV basis coefficient line integrals.

For example, the system may be configured to receive image data of an energy-resolved sinogram as input, and configured to produce a set of at least two tomographic basis images.

Preferably, the system may be configured to produce said tomographic basis images by minimizing a penalized data discrepancy between the forward projection of the basis images and said energy-resolved sinogram.

The system may also be configured to acquire at least one tomographic image and at least one projection image and where the basis decomposition is performed on at least the projection image(s).

An imaging system, such as the one illustrated in FIG. 4, may comprise a system for processing a radiographic image as described above. In an example embodiment, the invention is implemented on the computer and applied on the raw data after readout. In another example embodiment of the invention, the algorithm is implemented in the digital processing circuitry, or optionally a combination thereof.

In a particular example, at least some of the steps, functions, procedures, modules and/or blocks described herein are implemented in a computer program, which is loaded into the memory for execution by the processing circuitry.

Figure 11:
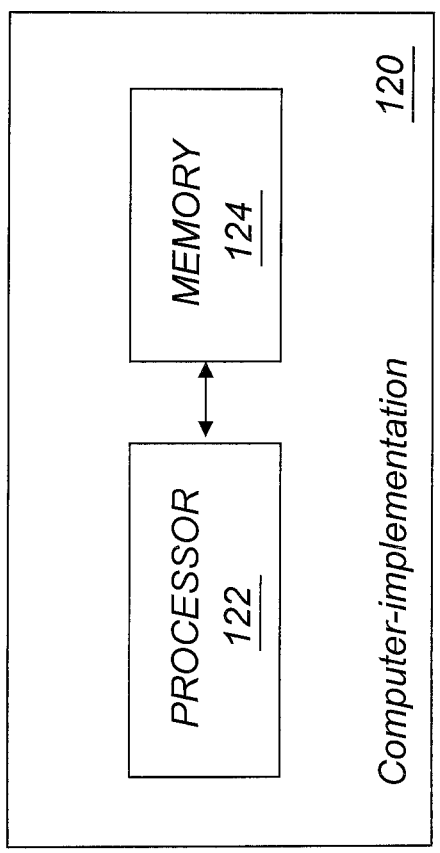
FIG. 11 is a schematic diagram illustrating an example of a computer-implementation of the proposed technology for processing a radiographic image.

FIG. 11 is a schematic diagram illustrating an example of a computer-implementation of the proposed technology for processing a radiographic image. The system 120 for processing a radiographic image comprises a processor 122 and a memory 124. The processor 122 and memory 124 are interconnected to each other to enable normal software execution. An optional input/output device may also be interconnected to the processor and/or the memory to enable input and/or output of relevant data such as input parameter(s) and/or resulting output parameter(s).

The term 'computer' should be interpreted in a general sense as any system or device capable of executing program code or computer program instructions to perform a particular processing, determining or computing task.

In a particular example, the computer program comprises instructions, which when executed by at least one processor, cause the processor(s) to:
provide energy-resolved image data representative of a radiographic image acquired with at least two energy levels; and
perform basis decomposition of said provided image data into at least one basis image representation by using at least one ordinary basis function modeling a physical material and at least one basis function modeling the Non-Linear Partial Volume, NLPV, effect.

The software or computer program may be realized as a computer program product, which is normally carried or stored on a computer-readable medium. The computer-readable medium may include one or more removable or non-removable memory devices including, but not limited to a Read-Only Memory, ROM, a Random Access Memory, RAM, a Compact Disc, CD, a Digital Versatile Disc, DVD, a Universal Serial Bus, USB, memory, a Hard Disk Drive, HDD storage device, a flash memory, or any other conventional memory device. The computer program may thus be loaded into the operating memory of a computer or equivalent processing device for execution by the processing circuitry thereof.

For example, the computer program stored in memory includes program instructions executable by the processing circuitry, whereby the processing circuitry is able or operative to execute the above-described steps, functions, procedure and/or blocks.

The computer or processing circuitry does not have to be dedicated to only execute the above-described steps, functions, procedure and/or blocks, but may also execute other tasks.

The embodiments described above are merely given as examples, and it should be understood that the proposed technology is not limited thereto. It will be understood by those skilled in the art that various modifications, combinations and changes may be made to the embodiments without departing from the present scope as defined by the appended claims. In particular, different part solutions in the different embodiments can be combined in other configurations, where technically possible. For example, the forward model in Eq. 8, which relates basis projection line integrals to registered counts may be modified to include scattered photons or detector imperfections such as charge sharing, pileup or scintillator lag. Alternatively, the analytical forward model in Eq. 8 may be replaced by a lookup table based on measurements of the number of registered counts for different combinations of materials traversed by the beam. Furthermore, the data discrepancy expressions in e.g. Eq. 2 and Eq. 23 may be modified to take count number correlations between energy bins into account. Also, the average over the extent of the beam in Eq. 4 may be replaced by a weighted average, modeling non-uniform intensity of the x-ray source.

The invention claimed is:

1. An image processing method for medical imaging including processing a radiographic image acquired with at least two energy levels, said method comprising the steps of:
providing (S1), to a processing circuitry and memory, energy-resolved image data, either from a detector or from an intermediate data storage, the energy-resolved image data representative of said radiographic image with at least two energy levels; and
generating, by way of the processing circuitry and memory, at least one image representation for medical imaging by decomposing (S2) said provided image data into at least one basis image representation, based on a model where a combination of at least two basis functions is used to express a representation of at least one linear attenuation coefficient, where at least one ordinary basis function models a physical material, and an NLPV basis function models the Non-Linear Partial Volume (NLPV) effect,
wherein said at least one other basis function that models the NLPV effect is constructed by:
selecting (S11) a set of at least one ordinary basis function, such that the energy dependent linear attenuation coefficients of homogeneous materials in the image volume can be described by a linear combination of the basis functions in the set,
determining (S12) the fraction of transmitted photons as a function of energy for a detector element situated behind an inhomogeneous region of materials, as seen from the source, taking into account the spatially extended nature of either the detector, the source or both, and
determining (S13) at least one NLPV basis function as the linear attenuation coefficient of a fictious material which, if one unit of distance of a homogeneous slab of this material were traversed by an x-ray beam, would give the same transmitted photon fraction as a function of energy as said calculated fraction which is transmitted through an inhomogeneous region.

2. A computer program product comprising a non-transitory computer-readable storage medium having recorded thereon a computer program, wherein the computer program comprises instructions which, when executed by at least one processor, cause the processor(s) to carry out the steps of claim 1.

3. A system (120) for medical imaging based on processing a radiographic image acquired with at least two energy levels, said system comprises:
processing circuitry and memory, the memory comprising instruction code executable by the processing circuitry, whereby upon execution of the instruction code, the processing circuitry is operative to:
obtain energy-resolved image data representative of said radiographic image with at least two energy levels by receiving image data of an energy-resolved sinogram as input, and
generate at least one image representation for medical imaging by performing basis decomposition of said image data into at least one basis image representation, based on a model where a combination of at least two basis functions is used to express a representation of at least one linear attenuation coefficient, where at least one basis function, also referred to as an ordinary basis function, models a physical material and at least one other basis function, also referred to as an NLPV basis function, models the Non-Linear Partial Volume, NLPV, effect to produce at least one basis image corresponding to an NLPV basis function, also referred to as an NLPV basis image, or at least one subsequently reconstructed tomographic NLPV basis image, enabling the identification of interface.

4. An image processing method for medical imaging including processing a radiographic image acquired with at least two energy levels, said method comprising the steps of:
providing (S1), to a processing circuitry and memory, energy-resolved image data, either from a detector or from an intermediate data storage, the energy-resolved image data representative of said radiographic image with at least two energy levels; and
generating, by way of the processing circuitry and memory, at least one image representation for medical imaging by decomposing (S2) said provided image data into at least one basis image representation, based on a model where a combination of at least two basis functions is used to express a representation of at least one linear attenuation coefficient, where at least one ordinary basis function models a physical material, and an NLPV basis function models the Non-Linear Partial Volume (NLPV) effect,
wherein the provided image data is an energy-resolved sonogram, and the output is either of an NLPV basis image corresponding to an NLPV basis function or a subsequently reconstructed tomographic NLPV basis image, said output enabling the identification of interfaces.

5. A computer program product comprising a non-transitory computer-readable storage medium having recorded thereon a computer program, wherein the computer program comprises instructions which, when executed by at least one processor, cause the processor(s) to carry out the steps of claim 4.

6. An image processing method for medical imaging including processing a radiographic image acquired with at least two energy levels, said method comprising the steps of:
providing (S1), to a processing circuitry and memory, energy-resolved image data, either from a detector or from an intermediate data storage, the energy-resolved image data representative of said radiographic image with at least two energy levels; and
generating, by way of the processing circuitry and memory, at least one image representation for medical imaging by decomposing (S2) said provided image data into at least one basis image representation, based on a model where a combination of at least two basis functions is used to express a representation of at least one linear attenuation coefficient, where at least one ordinary basis function models a physical material, and an NLPV basis function models the Non-Linear Partial Volume (NLPV) effect,
wherein the provided image data is an energy-resolved sonogram, and the output is at least one ordinary basis image corresponding to an ordinary basis function, which is subsequently reconstructed to yield at least one tomographic ordinary basis image, and
wherein said at least one tomographic ordinary basis image has a reduced level of NLPV artifacts compared to a tomographic basis image reconstructed from a basis image resulting from a basis material decomposition without NLPV basis.

7. A computer program product comprising a non-transitory computer-readable storage medium having recorded thereon a computer program, wherein the computer program comprises instructions which, when executed by at least one processor, cause the processor(s) to carry out the steps of claim 6.

8. An image processing method for medical imaging including processing a radiographic image acquired with at least two energy levels, said method comprising the steps of:
providing (S1), to a processing circuitry and memory, energy-resolved image data, either from a detector or from an intermediate data storage, the energy-resolved image data representative of said radiographic image with at least two energy levels; and
generating, by way of the processing circuitry and memory, at least one image representation for medical imaging by decomposing (S2) said provided image data into at least one basis image representation, based on a model where a combination of at least two basis functions is used to express a representation of at least one linear attenuation coefficient, where at least one ordinary basis function models a physical material, and an NLPV basis function models the Non-Linear Partial Volume (NLPV) effect,
wherein the output basis image representation(s) include at least one sinogram of ordinary basis coefficient line integrals and at least one sinogram of NLPV basis coefficient line integrals, where subsequently a set of ordinary tomographic basis images corresponding to ordinary basis functions is computed by minimizing a penalized data discrepancy between said at least one sinogram of ordinary basis coefficient line integrals and said at least one sinogram of NLPV basis coefficient line integrals, on one side, and at least one sinogram of simulated ordinary basis coefficient line integrals obtained from a forward projection of said tomographic basis images, on the other side, where said forward projection is calculated with at least two line integrals from the source to each detector element, yielding a spatially variant basis coefficient line integral for each detector element, and where a mapping is used to translate a representation of said spatially variant basis coefficient line integrals into said at least one sinogram of simulated ordinary basis coefficient line integrals and said at least one sinogram of NLPV basis coefficient line integrals.

9. A computer program product comprising a non-transitory computer-readable storage medium having recorded thereon a computer program, wherein the computer program comprises instructions which, when executed by at least one processor, cause the processor(s) to carry out the steps of claim 8.

* * * * *